(12) United States Patent
Brady-Kalnay

(10) Patent No.: US 10,745,703 B2
(45) Date of Patent: Aug. 18, 2020

(54) COMPOSITIONS AND METHODS FOR TREATING CANCER

(71) Applicant: CASE WESTERN RESERVE UNIVERSITY, Cleveland, OH (US)

(72) Inventor: Susann Brady-Kalnay, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/873,528

(22) Filed: Oct. 2, 2015

(65) Prior Publication Data

US 2016/0083734 A1 Mar. 24, 2016

Related U.S. Application Data

(63) Continuation of application No. 13/390,494, filed as application No. PCT/US2010/045602 on Aug. 16, 2010, now Pat. No. 9,241,949.

(60) Provisional application No. 61/352,100, filed on Jun. 7, 2010, provisional application No. 61/234,221, filed on Aug. 14, 2009.

(51) Int. Cl.
| | |
|---|---|
| *C12N 15/113* | (2010.01) |
| *A61K 38/17* | (2006.01) |
| *A61K 47/64* | (2017.01) |
| *A61K 31/7105* | (2006.01) |
| *A61K 31/7088* | (2006.01) |
| *A61K 49/00* | (2006.01) |

(52) U.S. Cl.
CPC ...... *C12N 15/1138* (2013.01); *A61K 31/7088* (2013.01); *A61K 31/7105* (2013.01); *A61K 38/17* (2013.01); *A61K 47/64* (2017.08); *A61K 49/0002* (2013.01); *C12N 2310/14* (2013.01); *C12N 2310/3513* (2013.01); *C12N 2310/531* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 8,686,112 | B2 * | 4/2014 | Brady-Kalnay ... | A61K 49/0032 435/4 |
| 2003/0105000 | A1 * | 6/2003 | Pero ...................... | A61K 38/06 514/19.3 |
| 2009/0182134 | A1 * | 7/2009 | Khvorova .............. | C07H 21/00 536/23.1 |

OTHER PUBLICATIONS

Burgoyne et al. (Neuro-Oncology Mar. 20, 2009, 11:767-778).*
ATCC (U-87 MG (ATCC HTB-14, 2016).*
Ulbricht et al. (J. Neurochemistry 2006 98: 1497-1506).*
Craig and Brady-Kalnay (Anticancer Agents Med. Chem. Jan. 2011 11(1): 133-140).*
Zellner et al (Clin. Can. Res., 1998, 4:1797-1802).*
Dermer (Bio/Technology, 1994, 12:320).*
Zips et al. (In vivo, 2005, 19:1-7).*
Gura (Science, 1997, 278:1041-1042).*
Pei and Tuschl (Nature Methods, 2006, 3: 670-676).*
Kaiser (Science, 2006, 313: 1370).*
Gerdes et al. (Front. Oncol. Dec. 18, 2014 doi: 10.3389/fonc.2014.00366, pp. 1-12).*
Krontiris and Capizzi (Internal Medicine, 4th Edition, Editor-in-chief Jay Stein, Elsevier Science, 1994 Chapters 71-72, pp. 699-729).*
Bowie et al. (Science, 1990, 247:1306-1310).*
Ibragimova and Wade (Biophysical Journal, Oct. 1999, vol. 77, pp. 2191-2198).*
Burgess et al. (J. of Cell Bio. 111:2129-2138, 1990).*

* cited by examiner

*Primary Examiner* — Peter J Reddig
(74) *Attorney, Agent, or Firm* — Tarolli, Sundheim, Covell & Tummino LLP

(57) ABSTRACT

A method of one or more of, inhibiting motility, migration, dispersal, and metastasis of a cell that expresses an RPTP, which is proteolytically cleaved to form intracellular fragments in the cell includes administering to the cell an amount of an agent effective to inhibit one or more of the catalytic activity and function of the proteolytically cleaved intracellular domain-containing fragments of the RPTP.

28 Claims, 25 Drawing Sheets

Specification includes a Sequence Listing.

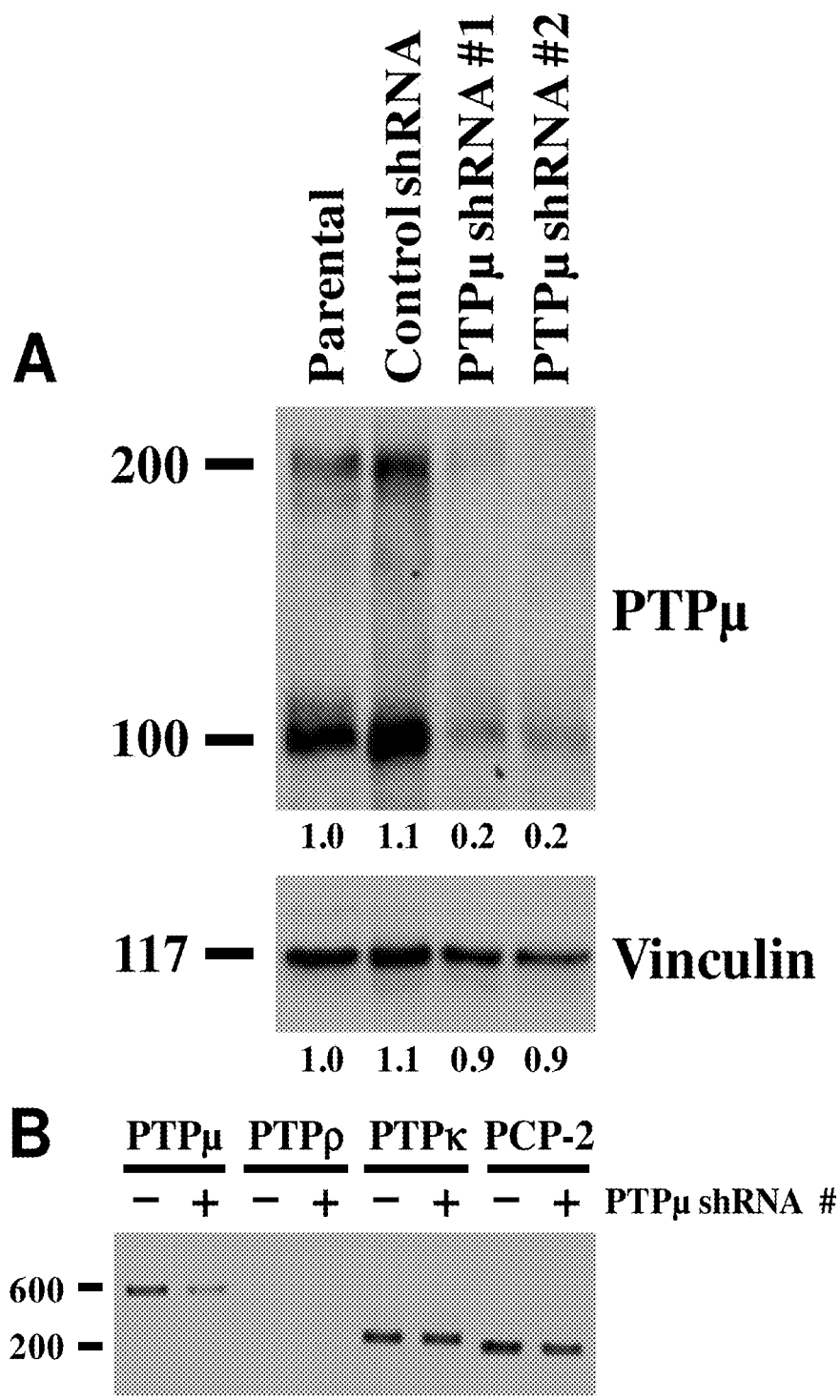
Fig. 3A-B

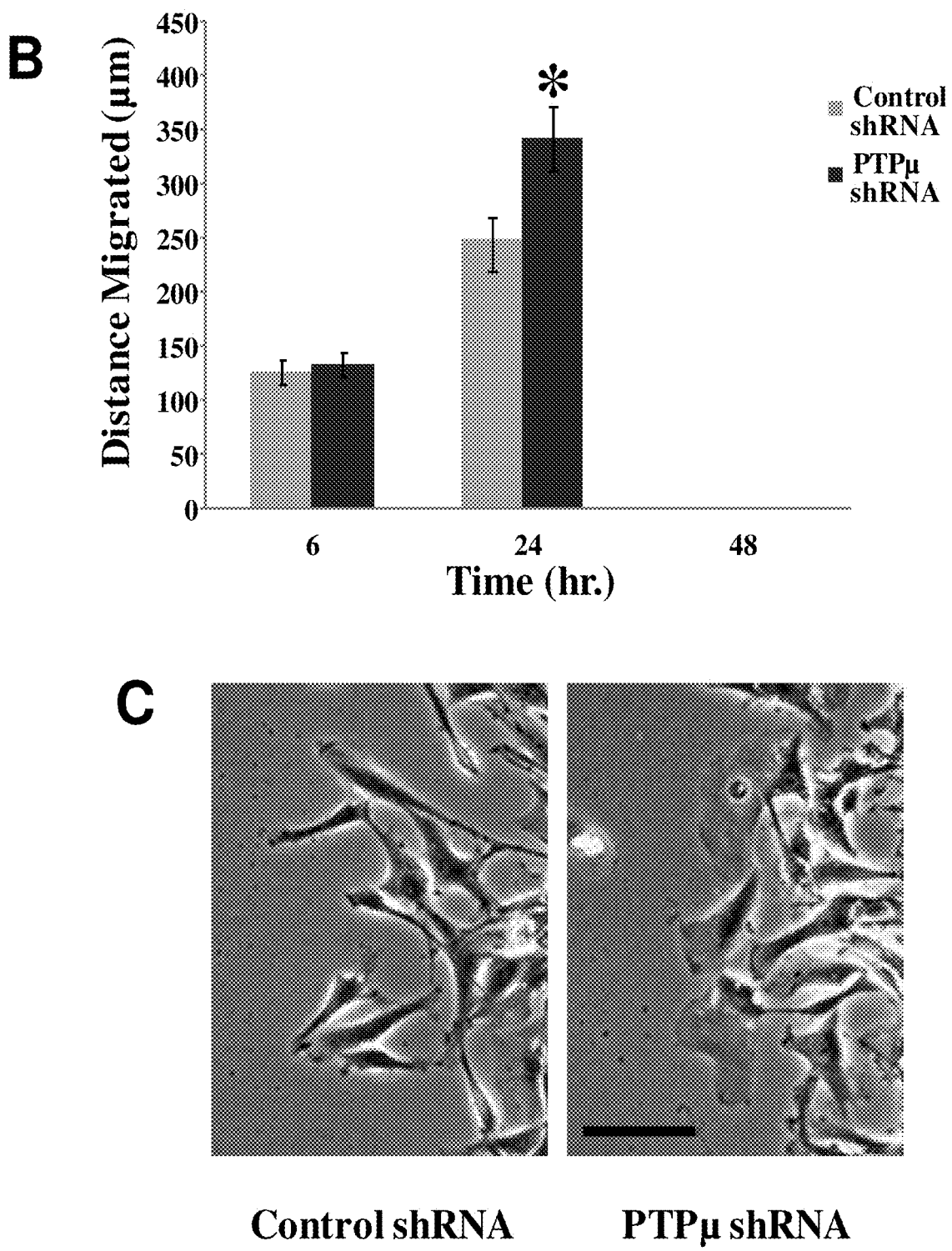
Fig. 4B-C

A Control shRNA  PTPμ shRNA #1  PTPμ shRNA #2
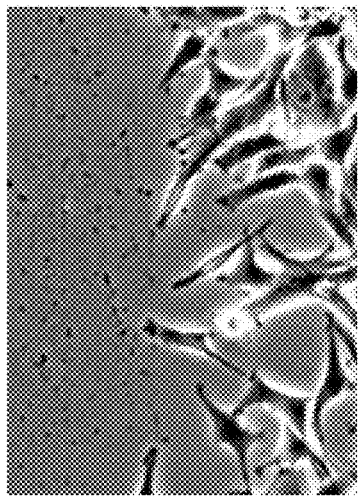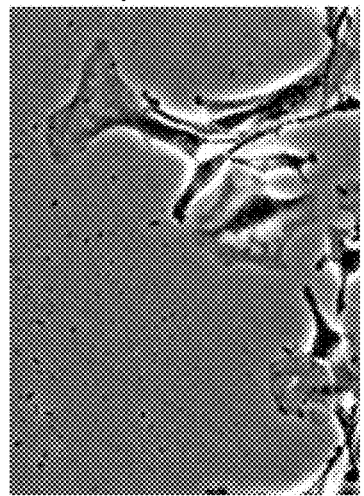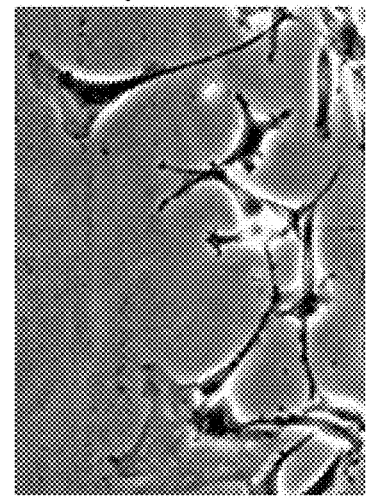
B Control shRNA  PTPμ shRNA #1
Vehicle
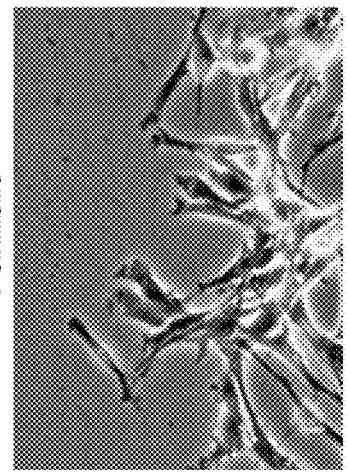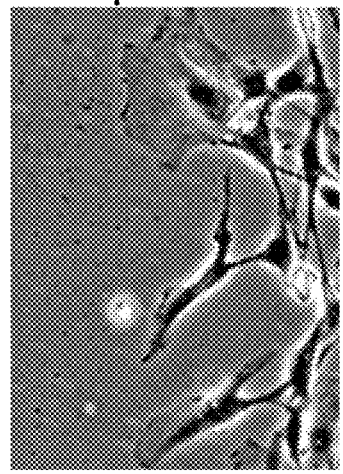
Rac1 Inhibitor
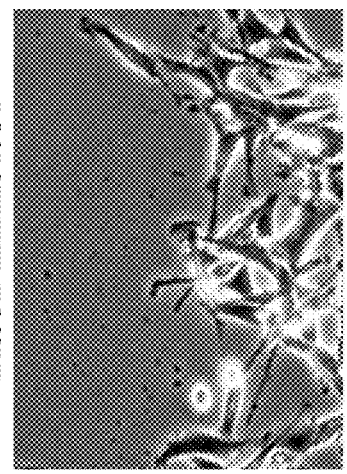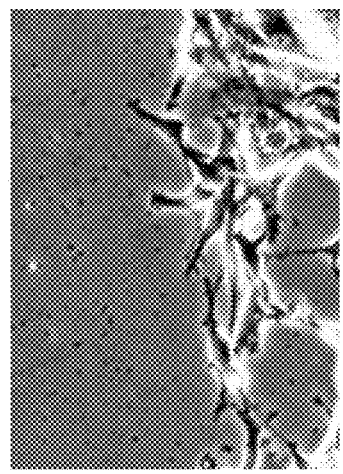
Fig. 5A-B

A
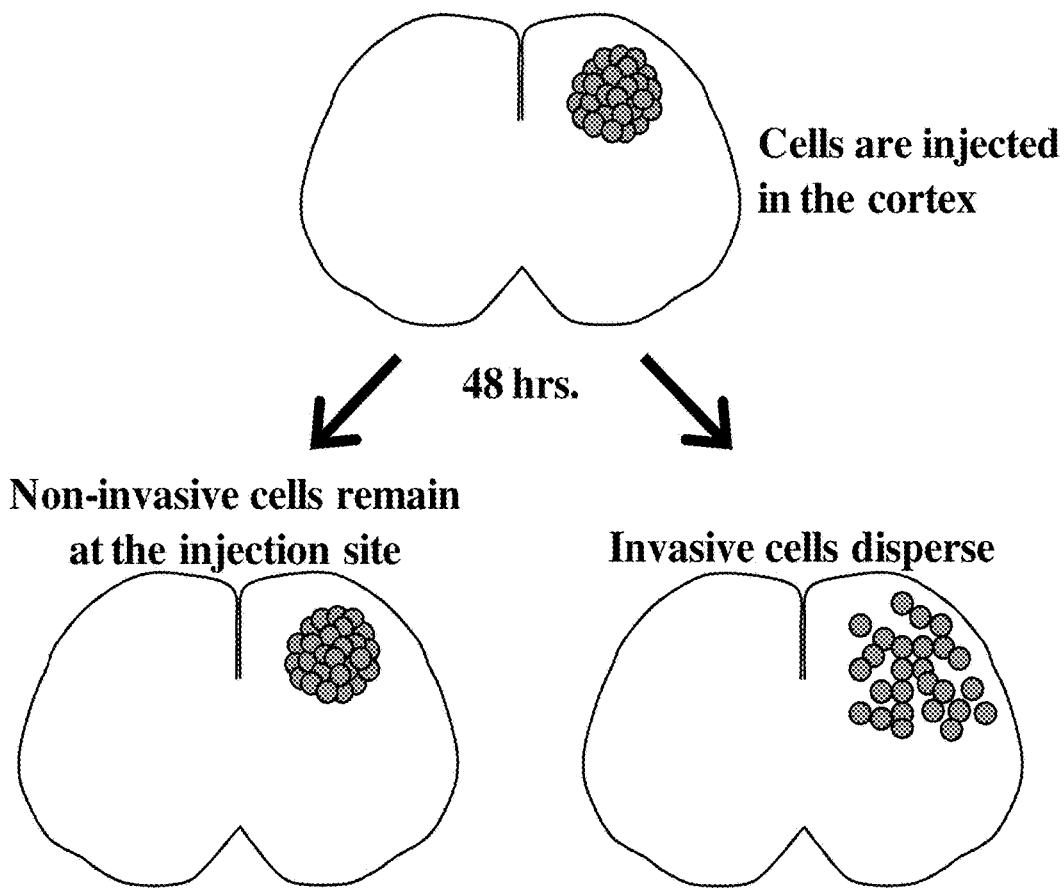
B
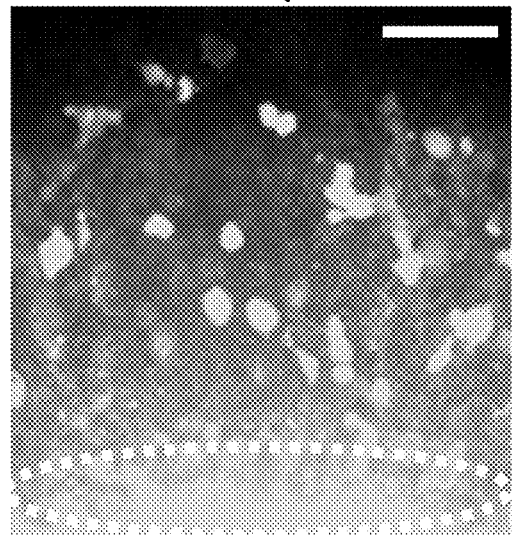
Fig. 7A-B

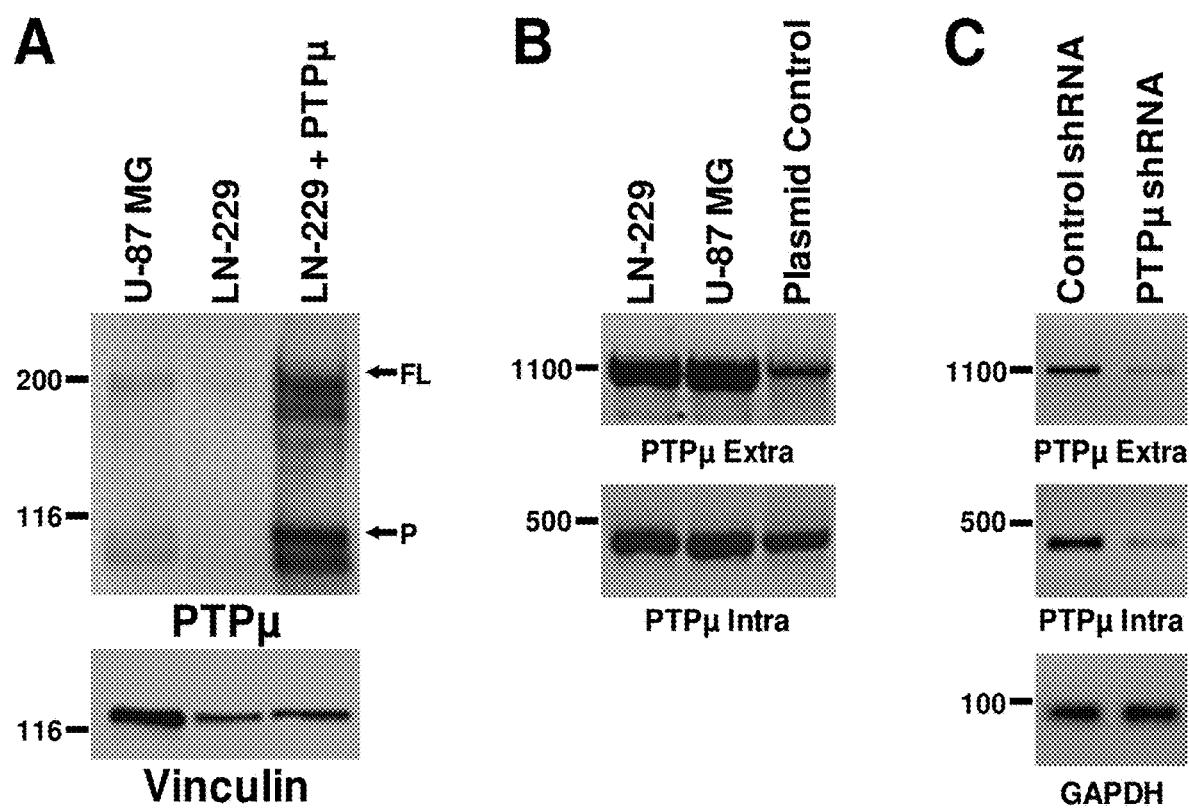
Figs. 9A-C

A
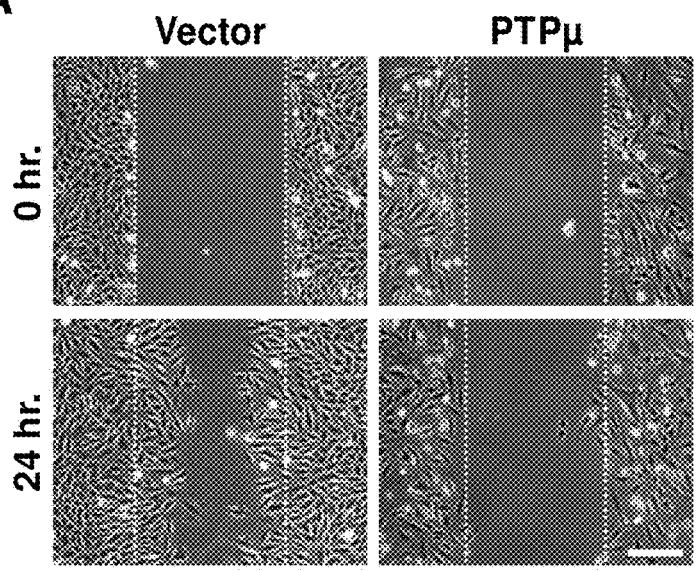 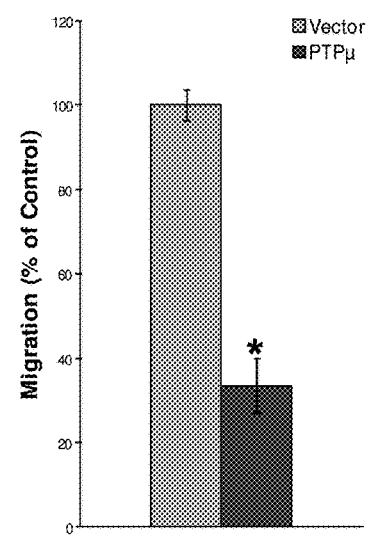
B
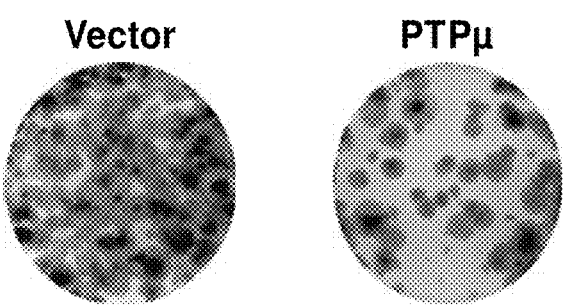 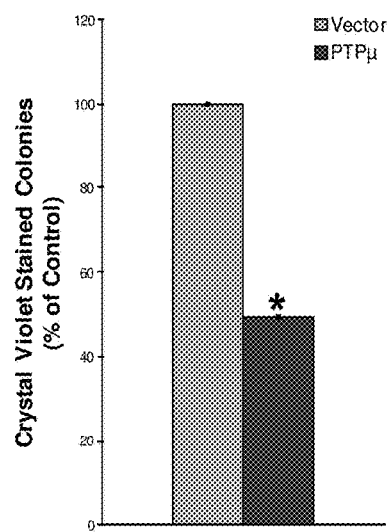
Figs. 10A-B

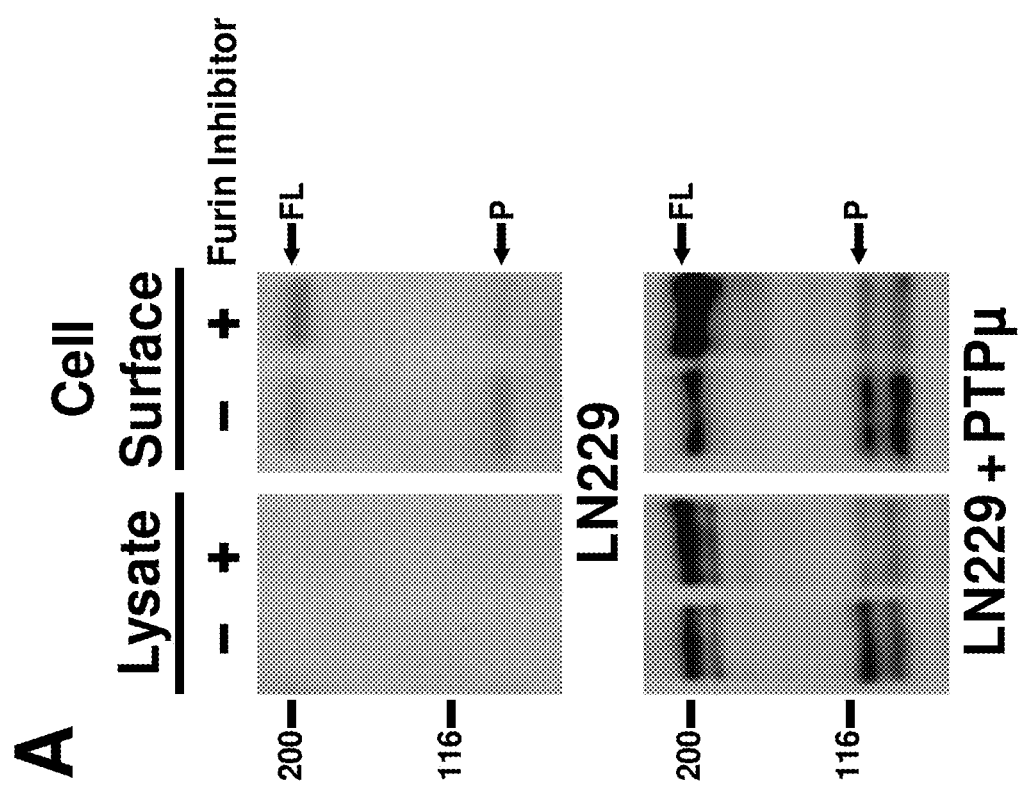
Fig. 11A-B

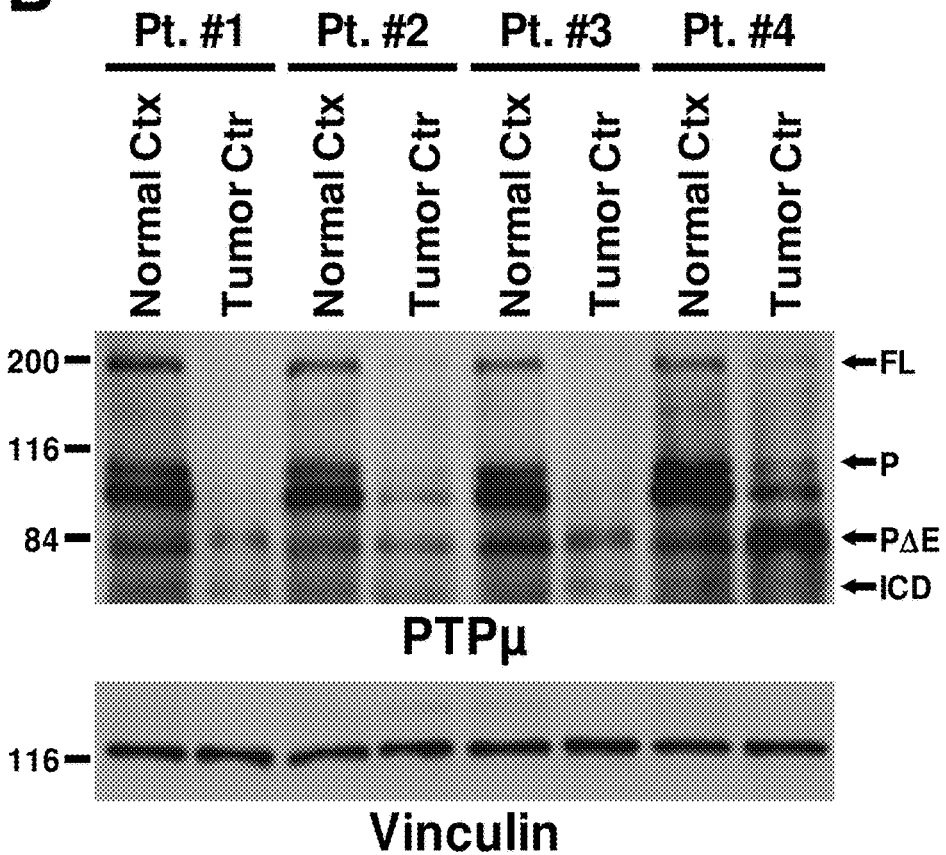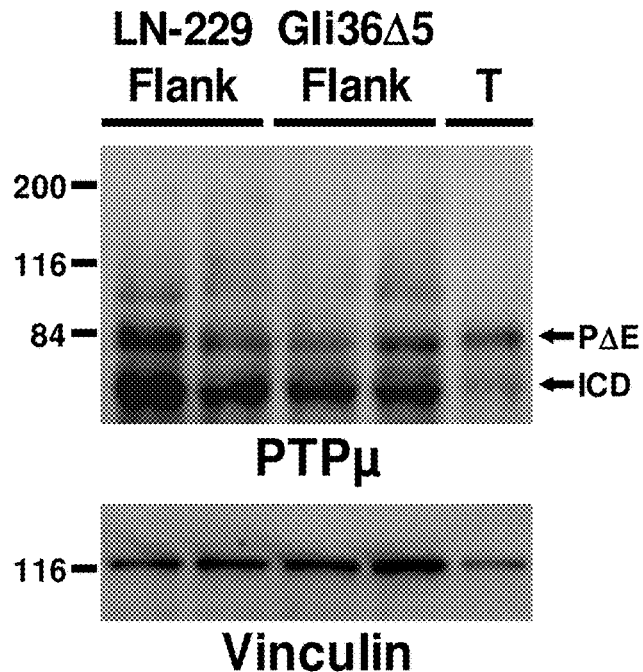
Fig. 12B-C

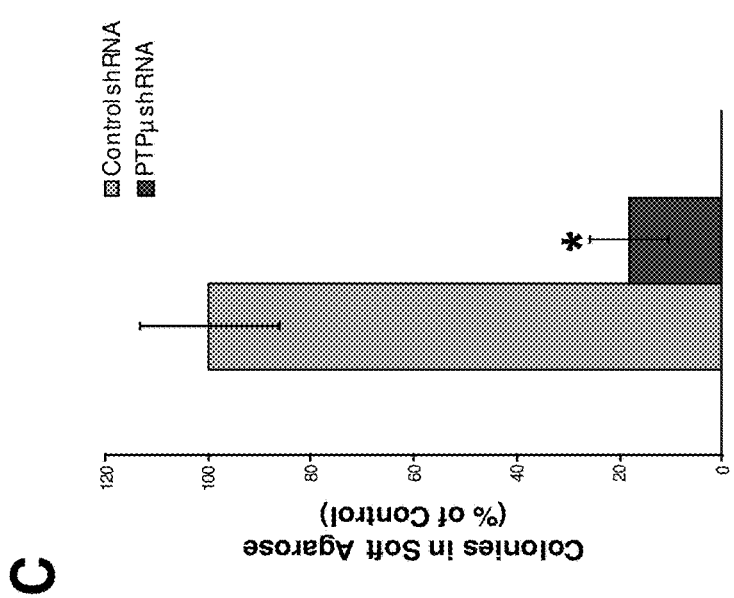
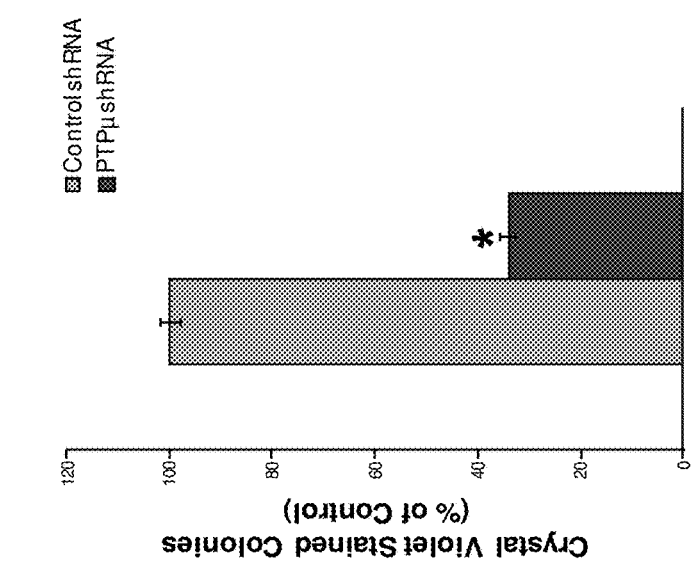
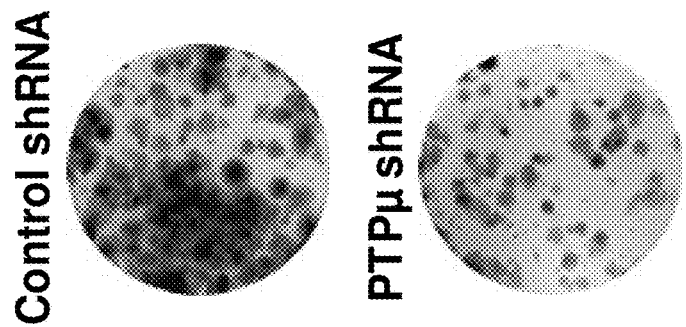
Fig. 13B-C

Human Prostate Tumor Cell line Xenografts

Human Melanomas show variable cleavage of PTPmu

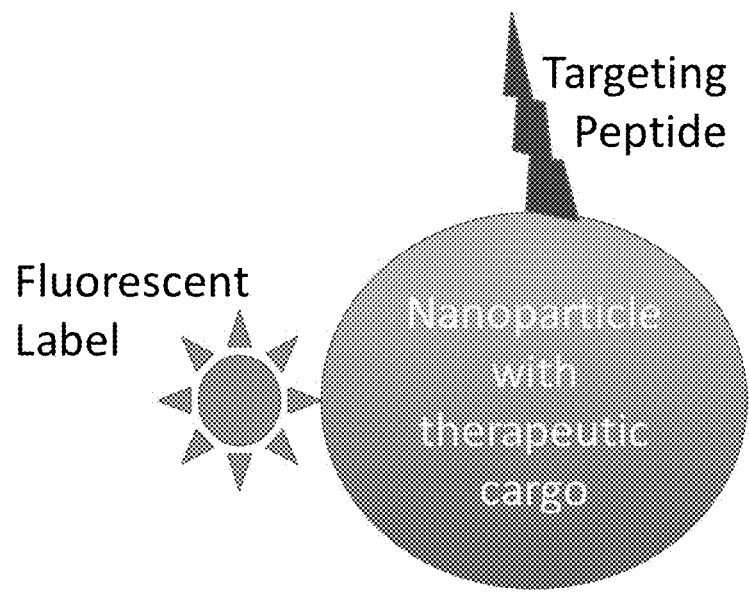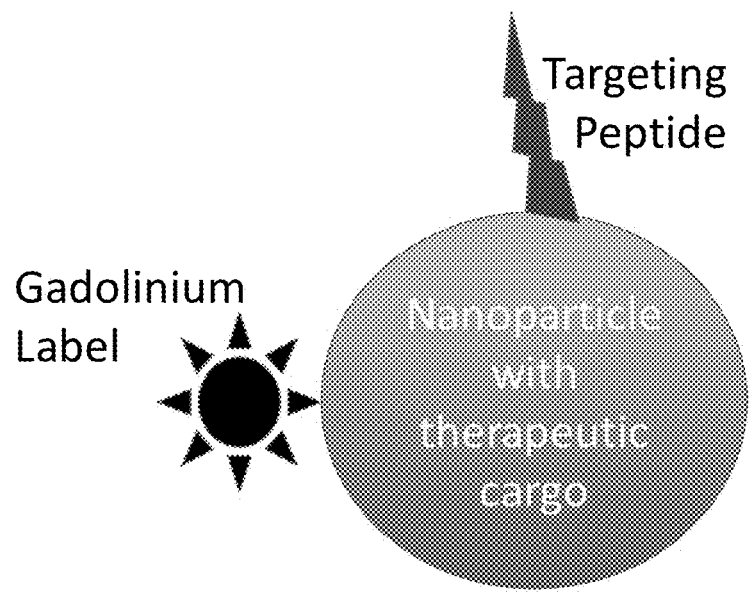
Figs. 18A-B

SEQUENCE LISTING

<160> NUMBER OF SEQ ID NOS: 23

<210> SEQ ID NO 1
<211> LENGTH: 1465
<212> TYPE: PRT
<213> ORGANISM: Homo sapiens

<400> SEQUENCE: 1

```
Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95
```

```
Ile Asp Phe His Tyr Phe Val Ser Ser Lys Ser Asn Ser Pro Pro Gly
                100                 105                 110

Leu Leu Asn Val Tyr Val Lys Val Asn Asn Gly Pro Leu Gly Asn Pro
115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
        165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
            245                 250                 255

Lys Tyr Arg Cys Met Ile Arg Thr Glu Gly Gly Val Gly Ile Ser Asn
                260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
            290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
            420                 425                 430

Val Ser Trp Asp Thr Glu Asn Ser His Pro Gln His Thr Ile Thr Asn
    435                 440                 445

Leu Ser Pro Tyr Thr Asn Val Ser Val Lys Leu Ile Leu Met Asn Pro
        450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
            500                 505                 510
```

```
Ile Thr Leu Tyr Glu Ile Thr Tyr Lys Ala Val Ser Ser Phe Asp Pro
            515                 520                 525

Glu Ile Asp Leu Ser Asn Gln Ser Gly Arg Val Ser Lys Leu Gly Asn
            530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
            565                 570                 575

Asn Gln Phe Thr Thr Lys Ile Ser Ala Pro Ser Met Pro Ala Tyr Glu
            580                 585                 590

Leu Glu Thr Pro Leu Asn Gln Thr Asp Asn Thr Val Thr Val Met Leu
            595                 600                 605

Lys Pro Ala His Ser Arg Gly Ala Pro Val Ser Val Tyr Gln Ile Val
            610                 615                 620

Val Glu Glu Glu Arg Pro Arg Arg Thr Lys Lys Thr Thr Glu Ile Leu
625                 630                 635                 640

Lys Cys Tyr Pro Val Pro Ile His Phe Gln Asn Ala Ser Leu Leu Asn
            645                 650                 655

Ser Gln Tyr Tyr Phe Ala Ala Glu Phe Pro Ala Asp Ser Leu Gln Ala
            660                 665                 670

Ala Gln Pro Phe Thr Ile Gly Asp Asn Lys Thr Tyr Asn Gly Tyr Trp
            675                 680                 685

Asn Thr Pro Leu Leu Pro Tyr Lys Ser Tyr Arg Ile Tyr Phe Gln Ala
            690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
            725                 730                 735

Thr Asp His Thr Val Lys Ile Ala Gly Val Ile Ala Gly Ile Leu Leu
            740                 745                 750

Phe Val Ile Ile Phe Leu Gly Val Val Leu Val Met Lys Lys Arg Lys
            755                 760                 765

Leu Ala Lys Lys Arg Lys Glu Thr Met Ser Ser Thr Arg Gln Glu Met
            770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
            805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Pro Phe Val Pro Thr
            835                 840                 845

Ala Ile Leu Val Pro Ile Asn Asp Glu Thr His Thr Met Ala Ser Asp
850                 855                 860

Thr Ser Ser Leu Val Gln Ser His Thr Tyr Lys Lys Arg Glu Pro Ala
865                 870                 875                 880

Asp Val Pro Tyr Gln Thr Gly Gln Leu His Pro Ala Ile Arg Val Ala
            885                 890                 895

Asp Leu Leu Gln His Ile Thr Gln Met Lys Cys Ala Glu Gly Tyr Gly
            900                 905                 910

Phe Lys Glu Glu Tyr Glu Ser Phe Phe Glu Gly Gln Ser Ala Pro Trp
            915                 920                 925

Asp Ser Ala Lys Lys Asp Glu Asn Arg Met Lys Asn Arg Tyr Gly Asn
```

-continued

```
                930             935             940
Ile Ile Ala Tyr Asp His Ser Arg Val Arg Leu Gln Thr Ile Glu Gly
945                 950             955             960

Asp Thr Asn Ser Asp Tyr Ile Asn Gly Asn Tyr Ile Asp Gly Tyr His
                965             970             975

Arg Pro Asn His Tyr Ile Ala Thr Gln Gly Pro Met Gln Glu Thr Ile
            980             985             990

Tyr Asp Phe Trp Arg Met Val Trp His Glu Asn Thr Ala Ser Ile Ile
        995             1000            1005

Met Val Thr Asn Leu Val Glu Val Gly Arg Val Lys Cys Cys Lys
    1010            1015            1020

Tyr Trp Pro Asp Asp Thr Glu Ile Tyr Lys Asp Ile Lys Val Thr
    1025            1030            1035

Leu Ile Glu Thr Glu Leu Leu Ala Glu Tyr Val Ile Arg Thr Phe
    1040            1045            1050

Ala Val Glu Lys Arg Gly Val His Glu Ile Arg Glu Ile Arg Gln
    1055            1060            1065

Phe His Phe Thr Gly Trp Pro Asp His Gly Val Pro Tyr His Ala
    1070            1075            1080

Thr Gly Leu Leu Gly Phe Val Arg Gln Val Lys Ser Lys Ser Pro
    1085            1090            1095

Pro Ser Ala Gly Pro Leu Val Val His Cys Ser Ala Gly Ala Gly
    1100            1105            1110

Arg Thr Gly Cys Phe Ile Val Ile Asp Ile Met Leu Asp Met Ala
    1115            1120            1125

Glu Arg Glu Gly Val Val Asp Ile Tyr Asn Cys Val Arg Glu Leu
    1130            1135            1140

Arg Ser Arg Arg Val Asn Met Val Gln Thr Glu Glu Gln Tyr Val
    1145            1150            1155

Phe Ile His Asp Ala Ile Leu Glu Ala Cys Leu Cys Gly Asp Thr
    1160            1165            1170

Ser Val Pro Ala Ser Gln Val Arg Ser Leu Tyr Tyr Asp Met Asn
    1175            1180            1185

Lys Leu Asp Pro Gln Thr Asn Ser Ser Gln Ile Lys Glu Glu Phe
    1190            1195            1200

Arg Thr Leu Asn Met Val Thr Pro Thr Leu Arg Val Glu Asp Cys
    1205            1210            1215

Ser Ile Ala Leu Leu Pro Arg Asn His Glu Lys Asn Arg Cys Met
    1220            1225            1230

Asp Ile Leu Pro Pro Asp Arg Cys Leu Pro Phe Leu Ile Thr Ile
    1235            1240            1245

Asp Gly Glu Ser Ser Asn Tyr Ile Asn Ala Ala Leu Met Asp Ser
    1250            1255            1260

Tyr Lys Gln Pro Ser Ala Phe Ile Val Thr Gln His Pro Leu Pro
    1265            1270            1275

Asn Thr Val Lys Asp Phe Trp Arg Leu Val Leu Asp Tyr His Cys
    1280            1285            1290

Thr Ser Val Val Met Leu Asn Asp Val Asp Pro Ala Gln Leu Cys
    1295            1300            1305

Pro Gln Tyr Trp Leu Glu Asn Gly Val His Arg His Gly Pro Ile
    1310            1315            1320

Gln Val Glu Phe Val Ser Ala Asp Leu Glu Glu Asp Ile Ile Ser
    1325            1330            1335
```

Arg Ile Phe Arg Ile Tyr Asn Ala Ala Arg Pro Gln Asp Gly Tyr
    1340                1345                1350

Arg Met Val Gln Gln Phe Gln Phe Leu Gly Trp Pro Met Tyr Arg
    1355                1360                1365

Asp Thr Pro Val Ser Lys Arg Ser Phe Leu Lys Leu Ile Arg Gln
    1370                1375                1380

Val Asp Lys Trp Gln Glu Glu Tyr Asn Gly Gly Glu Gly Arg Thr
    1385                1390                1395

Val Val His Cys Leu Asn Gly Gly Arg Ser Gly Thr Phe Cys
    1400                1405                1410

Ala Ile Ser Ile Val Cys Glu Met Leu Arg His Gln Arg Thr Val
    1415                1420                1425

Asp Val Phe His Ala Val Lys Thr Leu Arg Asn Asn Lys Pro Asn
    1430                1435                1440

Met Val Asp Leu Leu Asp Gln Tyr Lys Phe Cys Tyr Glu Val Ala
    1445                1450                1455

Leu Glu Tyr Leu Asn Ser Gly
    1460                1465

<210> SEQ ID NO 2
<211> LENGTH: 23
<212> TYPE: PRT
<213> ORGANISM: Homo sapiens

<400> SEQUENCE: 2

Asp Leu Leu Gln His Ile Thr Gln Met Lys Cys Ala Glu Gly Tyr Gly
1               5                   10                  15

Phe Lys Glu Glu Tyr Glu Ser
            20

<210> SEQ ID NO 3
<211> LENGTH: 23
<212> TYPE: PRT
<213> ORGANISM: Artificial Sequence
<220> FEATURE:
<223> OTHER INFORMATION: SYNTHETIC CONSTRUCT

<400> SEQUENCE: 3

Asp Leu Leu Gln His Ile Thr Gln Met Lys Cys Ala Glu Gly Tyr Gly
1               5                   10                  15

Phe Lys Glu Glu Tyr Glu Ser
            20

<210> SEQ ID NO 4
<211> LENGTH: 11
<212> TYPE: PRT
<213> ORGANISM: Artificial Sequence
<220> FEATURE:
<223> OTHER INFORMATION: SYNTHETIC CONSTRUCT

<400> SEQUENCE: 4

Gly Arg Lys Lys Arg Arg Gln Arg Arg Arg Cys
1               5                   10

<210> SEQ ID NO 5
<211> LENGTH: 34
<212> TYPE: PRT
<213> ORGANISM: Artificial Sequence
<220> FEATURE:
<223> OTHER INFORMATION: SYNTHETIC CONSTRUCT

```
<400> SEQUENCE: 5

Asp Leu Leu Gln His Ile Thr Gln Met Lys Cys Ala Glu Gly Tyr Gly
1               5                   10                  15

Phe Lys Glu Glu Tyr Glu Ser Gly Arg Lys Lys Arg Arg Gln Arg Arg
            20                  25                  30

Arg Cys

<210> SEQ ID NO 6
<211> LENGTH: 18
<212> TYPE: DNA
<213> ORGANISM: Artificial Sequence
<220> FEATURE:
<223> OTHER INFORMATION: SYNTHETIC CONSTRUCT

<400> SEQUENCE: 6
gggaggagga cccaggac                                                 18

<210> SEQ ID NO 7
<211> LENGTH: 20
<212> TYPE: DNA
<213> ORGANISM: Artificial Sequence
<220> FEATURE:
<223> OTHER INFORMATION: SYNTHETIC CONSTRUCT

<400> SEQUENCE: 7
tgtacgtgtt gggtctccag                                               20

<210> SEQ ID NO 8
<211> LENGTH: 18
<212> TYPE: DNA
<213> ORGANISM: Artificial Sequence
<220> FEATURE:
<223> OTHER INFORMATION: SYNTHETIC CONSTRUCT

<400> SEQUENCE: 8
ccctcagcct gctcctga                                                 18

<210> SEQ ID NO 9
<211> LENGTH: 20
<212> TYPE: DNA
<213> ORGANISM: Artificial Sequence
<220> FEATURE:
<223> OTHER INFORMATION: SYNTHETIC CONSTRUCT

<400> SEQUENCE: 9
ccaccattca ccttcacgta                                               20

<210> SEQ ID NO 10
<211> LENGTH: 20
<212> TYPE: DNA
<213> ORGANISM: Artificial Sequence
<220> FEATURE:
<223> OTHER INFORMATION: SYNTHETIC CONSTRUCTS

<400> SEQUENCE: 10
aaactcggca tggatacgac                                               20

<210> SEQ ID NO 11
<211> LENGTH: 20
<212> TYPE: DNA
<213> ORGANISM: Artificial Sequence
<220> FEATURE:
<223> OTHER INFORMATION: SYNTHETIC CONSTRUCT

<400> SEQUENCE: 11
```
ggcatctcgg gtggtagata                                                   20

<210> SEQ ID NO 12
<211> LENGTH: 20
<212> TYPE: DNA
<213> ORGANISM: Artificial Sequence
<220> FEATURE:
<223> OTHER INFORMATION: SYNTHETIC CONSTRUCT

<400> SEQUENCE: 12
caggcccagt acgatgactt                                                   20

<210> SEQ ID NO 13
<211> LENGTH: 20
<212> TYPE: DNA
<213> ORGANISM: Artificial Sequence
<220> FEATURE:
<223> OTHER INFORMATION: SYNTHETIC CONSTRUCT

<400> SEQUENCE: 13
agctgaactg cacacagtgg                                                   20

<210> SEQ ID NO 14
<211> LENGTH: 29
<212> TYPE: DNA
<213> ORGANISM: Artificial Sequence
<220> FEATURE:
<223> OTHER INFORMATION: SYNTHETIC CONSTRUCT

<400> SEQUENCE: 14
cgcgaattct agagacgttc tcaggtggc                                         29

<210> SEQ ID NO 15
<211> LENGTH: 28
<212> TYPE: DNA
<213> ORGANISM: Artificial Sequence
<220> FEATURE:
<223> OTHER INFORMATION: SYNTHETIC CONSTRUCT

<400> SEQUENCE: 15
cccgcaagct tacttcttct cgcacttg                                          28

<210> SEQ ID NO 16
<211> LENGTH: 33
<212> TYPE: DNA
<213> ORGANISM: Artificial Sequence
<220> FEATURE:
<223> OTHER INFORMATION: SYNTHETIC CONSTRUCT

<400> SEQUENCE: 16
cgcggatcca aagagaccat gagcagcacc cga                                    33

<210> SEQ ID NO 17
<211> LENGTH: 36
<212> TYPE: DNA
<213> ORGANISM: Artificial Sequence
<220> FEATURE:
<223> OTHER INFORMATION: SYNTHETIC CONSTRUCT

<400> SEQUENCE: 17
ccggaattct catctgttct catctttctt agccga                                 36

<210> SEQ ID NO 18
<211> LENGTH: 361
<212> TYPE: PRT

<213> ORGANISM: Homo sapiens

<400> SEQUENCE: 18

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly
        355                 360

<210> SEQ ID NO 19
<211> LENGTH: 280
<212> TYPE: PRT
<213> ORGANISM: Homo sapiens

<400> SEQUENCE: 19

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Lys Ser Asn Ser Pro Pro Gly
            100                 105                 110

Leu Leu Asn Val Tyr Val Lys Val Asn Asn Gly Pro Leu Gly Asn Pro
            115                 120                 125

Ile Trp Asn Ile Ser Gly Asp Pro Thr Arg Thr Trp Asn Arg Ala Glu
        130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
        210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Val Gly Ile Ser Asn
            260                 265                 270

Tyr Ala Glu Leu Val Val Lys Glu
        275                 280

<210> SEQ ID NO 20
<211> LENGTH: 20
<212> TYPE: PRT
<213> ORGANISM: Homo sapiens

<400> SEQUENCE: 20

Glu Thr Phe Ser Gly Gly Cys Leu Phe Asp Glu Pro Tyr Ser Thr Cys
1               5                   10                  15

Gly Tyr Ser Gln
            20

<210> SEQ ID NO 21
<211> LENGTH: 20
<212> TYPE: PRT
<213> ORGANISM: Homo sapiens

<400> SEQUENCE: 21

Glu Thr Phe Ser Gly Gly Cys Leu Phe Asp Glu Pro Tyr Ser Thr Cys

```
1               5                   10                  15
Gly Tyr Ser Gln
            20

<210> SEQ ID NO 22
<211> LENGTH: 19
<212> TYPE: PRT
<213> ORGANISM: Homo sapiens

<400> SEQUENCE: 22

Thr Pro His Phe Leu Arg Ile Gln Asn Val Glu Val Asn Ala Gly Gln
1               5                   10                  15

Phe Ala Thr

<210> SEQ ID NO 23
<211> LENGTH: 18
<212> TYPE: PRT
<213> ORGANISM: Homo sapiens

<400> SEQUENCE: 23

Gly Ile Asp Val Arg Asp Ala Pro Leu Lys Glu Ile Lys Val Thr Ser
1               5                   10                  15

Ser Arg
```

COMPOSITIONS AND METHODS FOR TREATING CANCER

RELATED APPLICATION

This application is a Continuation of U.S. application Ser. No. 13/390,494, filed Feb. 14, 2012, issued as U.S. Pat. No.: 9,241,949, which is a National Phase filing of PCT/US2010/045602, filed Aug. 16, 2010, which claims priority from U.S. Provisional Application Nos. 61/234,221, filed Aug. 14, 2009, and 61/352,100, filed Jun. 7, 2010, the subject matter of which are incorporated herein by reference in their entirety.

This application incorporates by reference a text (.txt) copy of the Sequence Listing. The name of the ASCII text file is CWR019301USPCTSEQUENCELSITING.TXT, created Nov. 19, 2010 and is 22.4 kb.

BACKGROUND

Cancer is a worldwide problem. Finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Typically, the surgical excision of large tumor masses is followed by chemotherapy and/or radiation therapy.

Cancer starts as a primary tumor at a single location. The primary tumor rarely causes death as it is usually surgically removed. Once cancer cells move away from the primary tumor site (migration, dispersal, and invasion) and move to distant sites (metastasis) the cancer becomes more deadly. The migrating, dispersing and invading cancer cells can rarely be detected and must be treated by conventional chemotherapy. Conventional chemotherapy does not specifically target cancer cells but affects a number of rapidly dividing normal cells.

SUMMARY

This application relates to a method of inhibiting one or more of, motility, migration, dispersal, and metastasis of a cell that expresses a receptor protein tyrosine phosphatase (RPTP) that is proteolytically cleaved to form intracellular domain-containing fragments. The method includes administering to the cell an amount of a therapeutic effective to inhibit function of the proteolytically cleaved intracellular domain-containing fragments of the RPTP. The inhibition of function of the proteolytically cleaved intracellular domain-containing fragments of the RPTP inhibits one or more of, motility, migration, dispersal, and metastasis of the cell.

This application also relates to method of inhibiting one or more of, motility, migration, dispersal, and metastasis of a cancer cell that expresses one or more of, an RPTP type IIb and RPTP type IIa that is proteolytically cleaved to form intracellular domain-containing fragments. The method includes administering to the cancer cell in the subject an amount of a therapeutic agent effective to inhibit function of the proteolytically cleaved intracellular domain-containing fragments of either RPTP type IIb or RPTP type IIa or both. The inhibition of function of the proteolytically cleaved intracellular domain-containing fragments inhibits one or more of, motility, migration, dispersal, and metastasis of the cancer cell.

This application further relates to a method of inhibiting one or more of, motility, migration, and dispersal of glioblastoma multiforme cells. The method includes administering to the glioblastoma multiforme cells an amount of a therapeutic agent effective to inhibit function of proteolytically cleaved intracellular domain-containing fragments of PTPμ of the cancer cells. The inhibition of function of proteolytically cleaved intracellular domain-containing fragments of PTPμ inhibits one or more of, the motility, migration, and dispersal of the glioblastoma multiforme cells.

BRIEF DESCRIPTION OF THE DRAWINGS

FIGS. 3(A-B) illustrate immunoblots of PTPμ mRNA and protein levels are decreased by shRNA. Lysates from U-87 MG cells infected with control or PTPμ shRNA lentivirus were immunoblotted for PTPμ using the intracellular antibody SK-18 (A). PTPμ shRNA reduced PTPμ protein levels in comparison to uninfected and control shRNA-infected cells. Vinculin was used as a loading control. Densitometry values for PTPμ and vinculin are shown under each lane and were normalized to parental cells. The numbers on the left side of the immunoblot correspond to the molecular weight in kDa. RNA from U-87 MG cells expressing control or PTPμ shRNA was analyzed by RT-PCR for PTPμ, PTPρ, PTPκ, and PCP-2 expression (B). PTPμ mRNA levels were decreased by shRNA targeting PTPμ. PTPκ and PCP-2 mRNA levels were unaffected; PTPρ was not expressed. The numbers on the left side of the gel represent the PCR product size in basepairs.

FIGS. 9(A-C) illustrate images showing PTPμ expression is post-transcriptionally regulated. (A) Lysates from U-87 MG cells, parental LN-229 cells, and LN-229 cells overexpressing PTPμ were analyzed by immunoblotting. PTPμ was detected using an antibody to the intracellular domain (SK-18) that recognizes both the full-length (FL) (200 kDa) protein and the furin-cleaved P-subunit (P) containing the intracellular domain (100 kDa). U-87 MG cells express PTPμ, but LN-229 cells downregulated PTPμ protein. PTPμ was overexpressed in LN-229 cells. Vinculin (117 kDa) was used as a loading control. (B) RT-PCR analysis of LN-229 and U-87 MG mRNA indicated PTPμ mRNA is expressed in both cell lines when compared to the PCR product of a control PTPμ-containing plasmid with primers derived from both the extracellular and intracellular domains. Size is indicated in basepairs. (C) PTPμ shRNA but not control shRNA downregulated PTPμ transcript; however, there was no change in GAPDH mRNA.

FIGS. 10(A-B) illustrate images showing overexpression of PTPμ suppresses glioblastoma cell migration and growth factor-independent survival. (A) Confluent monolayers of LN-229 cells expressing vector or PTPμ were scratched and imaged at 0 and 24 hours. Dashed lines indicate the position of the wounded edge at 0 hours. The scale bar represents 200 μm. An asterisk indicates a statistically significant 3-fold reduction in migration (p<0.0001, n=4). (B) LN-229 cells expressing vector or PTPμ were deprived of growth factor stimulation and allowed to form colonies. An asterisk indicates a statistically significant 2-fold reduction in colony formation (p<0.0001, n=3).

LN-229 cells expressing control or PTPμ shRNA were deprived of growth factor stimulation and allowed to form colonies. An asterisk indicates a statistically significant reduction in colony formation (p<0.001, n=2). (C) Colonies of LN-229 cells expressing control or PTPμ shRNA were allowed to form in soft agarose over four weeks. An asterisk indicates a statistically significant reduction in colony formation (p<0.0001, n=20).

Figure 14:
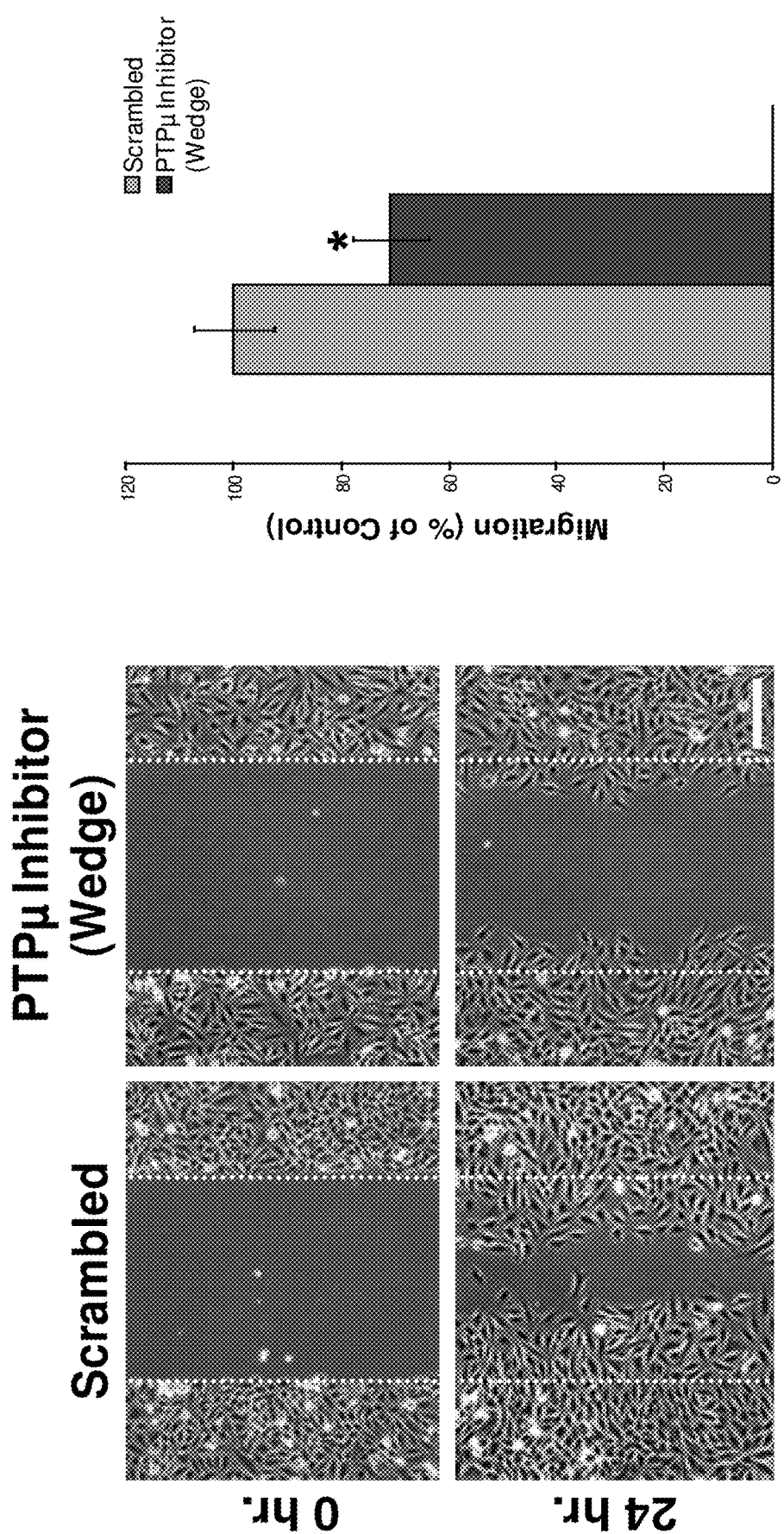

FIG. 14 illustrates images showing PTPμ fragment-induced migration of glioblastoma cells is abrogated by a peptide inhibitor of PTPμ function. Confluent monolayers of LN-229 cells were treated with the PTPμ wedge inhibitor peptide or a scrambled control, scratched to form a wound, and imaged at 0 and 24 hours. Dashed lines indicate the position of the wounded edge at 0 hours. The scale bar represents 200 μm. An asterisk indicates a statistically significant difference in migration (p<0.02, n=6).

Figure 15:
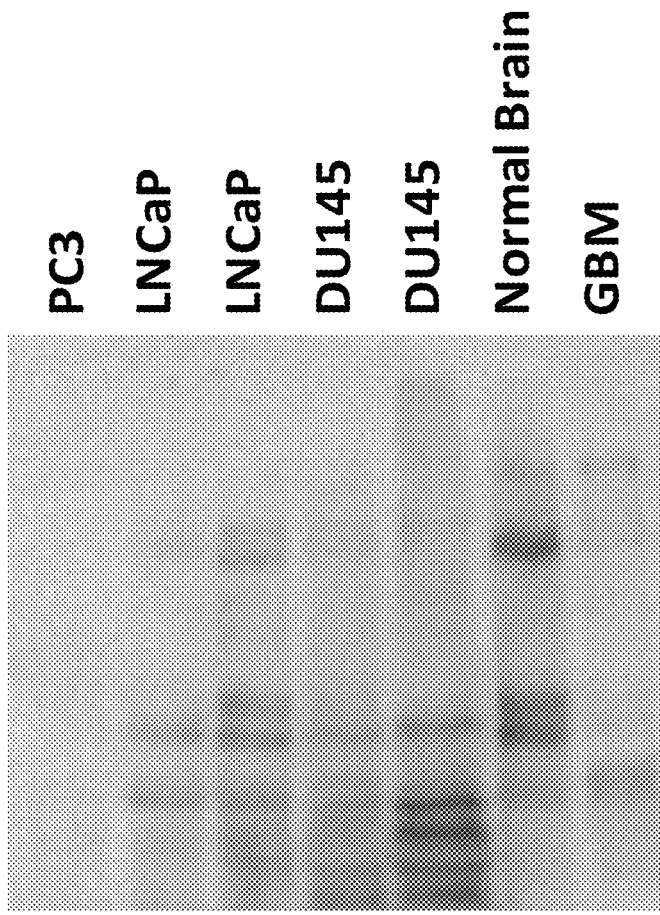

FIG. 15 illustrates an immunoassay showing the effects of Human Prostate Tumor Cell line Xenografts.

Figure 16:
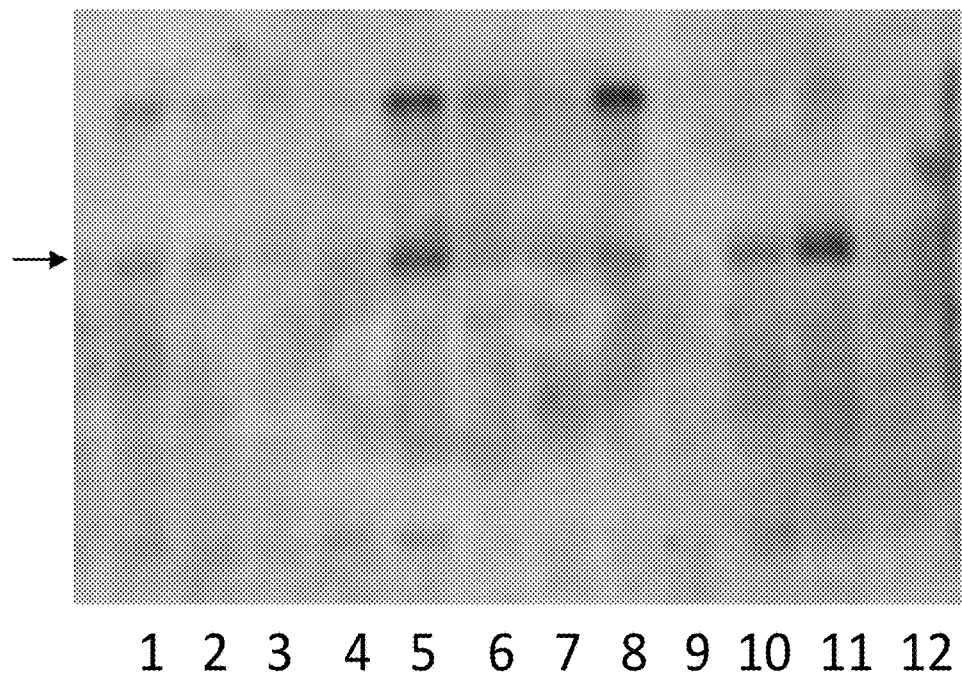

FIG. 16 illustrates an immunoblot showing the effects of Human Melanomas showing variable cleavage of PTPμ.

Figure 17:
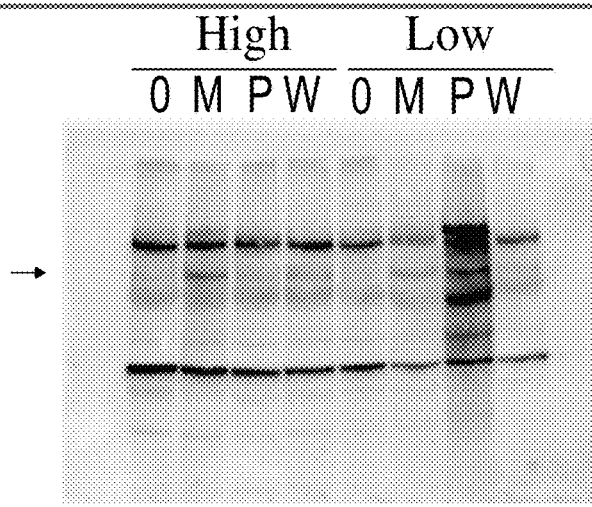

FIG. 17 illustrates an immunoblot showing the effects of PTPμ Fragment Generation in Lung Cancer Cells.

FIGS. 18(A-B) illustrate (A) the structure of the targeted nanoparticle conjugate containing a targeting peptide, the therapeutic cargo such as the therapeutic peptide, and a fluorophore imaging agent; and (B) the structure of the targeted nanoparticle conjugate containing a targeting peptide, the therapeutic cargo such as the therapeutic peptide and an MRI contrast imaging agent.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, "one or more of a, b, and c" means a, b, c, ab, ac, bc, or abc. The use of "or" herein is the inclusive or.

As used herein, "protein" is a polymer consisting of the 20 amino acids. Although "polypeptide" is often used in reference to relatively large polypeptides, and "peptide" is often used in reference to small polypeptides, usage of these terms in the art overlaps and is varied.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to changes in the genetic material of an organism, in particular a change (i.e., deletion, substitution, addition, or alteration) in a wild type polynucleotide sequence or changes in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue (e.g., the central nervous system), such that it enters the animal's system and, thus, is subject to metabolism and other like processes, for example, subcutaneous administration.

This application relates to compositions and methods of inhibiting one or more of, motility, migration, dispersal and metastases of cells, such as neoplastic, tumorgenic, and cancer cells, that express an RPTP that is proteolytically cleaved to produce intracellular domain (ICD) fragments, which can translocate to the nucleus and promote cell migration, motility, dispersal and metastasis.

Ig superfamily cell adhesion molecules, such as RPTP type IIb (e.g., PTPµ) and/or RPTP type IIa, are expressed by at least some cancer cells as a transmembrane protein that is proteolytically cleaved resulting in extracellular fragments that remains associated with the transmembrane and intracellular portion (P-subunit) through a non-covalent interaction (*J Biol Chem* 1994; 269: 28472-7; *Biochemistry* (Mosc) 1996; 35: 3797-802; J Cell Biol 1995; 131: 251-60). This cleavage can be mediated by a furin-like protease in the endoplasmic reticulum during intracellular trafficking (*Biochemistry* (Mosc) 1996; 35: 3797-802). Another type IIb RPTP, PTPκ, is also cleaved by a furin-like protease and further processed by an α-secretase of the A Disintegrin And Metalloproteinase domain (ADAM) family and a γ-secretase (*Mol Cell Biol* 2006; 26: 3917-34). The extracellular ADAM cleaves the P-subunit adjacent to the membrane to generate PΔE and shed the ectodomain. This cleavage primes PTPκ PΔE to be cleaved by γ-secretase, which releases the intracellular portion of PTPκ containing the active phosphatase domain from the membrane (*Mol Cell Biol* 2006; 26: 3917-34). The intracellular fragment of PTPκ translocates to the nucleus and controls β-catenin transcription.

In at least some cells expressing RPTPs, such as cancer cells including, for example glioblastoma cells, prostate cancer cells, melanoma cells, lung cancer cells and tumor-derived endothelial cells, both migration and growth factor-independent survival pathways are regulated by intracellular domain-containing fragments (or intracellular domain-containing fragments) of RPTPs, such as intracellular domain-containing fragments of either RPTP type IIb or RPTP type IIa or both. Agents or therapeutic agents that target and reduce and inhibit the function of the intracellular domain-containing fragments in these cells can be used to inhibit one or more of, the motility, migration, dispersal and metastases of these cells.

One aspect of this application relates to a method of inhibiting motility, migration, dispersal, and/or metastasis of a cancer cell that expresses an RPTP, which is proteolytically cleaved to form intracellular domain-containing fragments. The method includes administering to the cancer cell an amount of a therapeutic agent effective to inhibit one or more of, catalytic activity and function of the proteolytically cleaved intracellular domain-containing fragments of the RPTP. The inhibition of function of the proteolytically cleaved intracellular domain-containing fragments inhibits one or more of, motility, migration, dispersal, and metastasis of the cancer cell.

In one example, the RPTP can include a receptor protein tyrosine phosphatase (RPTP) type IIb or RPTP type IIa. In another example, RPTP can include PTPs of the type IIb subfamily, such as PTPµ, PTPκ, PTPρ, and PCP-2 (also called PTPλ). The intracellular domain of the RPTP type IIbs can include a juxtamembrane sequence with homology to cadherins and two phosphatase domains of which only the most membrane proximal is catalytically active (*Cell* 2004; 117: 699-711; *Biochem J* 2007; 402: 1-15). The juxtamembrane portion of PTPµ (SEQ ID NO: 1) contains a helix-loop-helix wedge-shaped motif having an amino acid sequence of SEQ ID NO: 2.

In certain embodiments, cancer cells that express an RPTP, which is proteolytically cleaved to produce intracellular domain-containing fragments that promote cancer cell motility, migration, and/or dispersal can include glioma cells. The term glioma, as used herein, refers to a type of cancer arising from glial cells in the brain or spine. Gliomas can be classified by cell type, by tumor grade, and by location. For example, ependymomas resemble ependymal cells, astrocytmoas (e.g., glioblastoma multiforme) resemble astrocytes, oligodedrogliomas resemble oligodendrocytes. Also mixed gliomas, such as oligoastrocytomas may contain cells from different types of glia. Gliomas can also be classified according to whether they are above or below a membrane in the brain called the tentorium. The tentorium separates the cerebrum, above, from the cerebellum, below. A supratentorial glioma is located above the tentorium, in the cerebrum, and occurs mostly in adults whereas an infratentorial glioma is located below the tentorium, in the cerebellum, and occurs mostly in children.

Other examples of cancer cells that express an RPTP, which can be proteolytically cleaved to produce intracellular domain-containing fragments that promotes cancer cell motility, migration, dispersal, and/or metastasis can include prostate cancer cells (FIG. 15), melanoma cells (FIG. 16), lung cancer cells (FIG. 17), and tumor-derived endothelial cells. Still other examples of cancer cells that express an RPTP, which can be proteolytically cleaved to produce intracellular domain-containing fragments that promotes cancer cell motility, migration, dispersal, and/or metastasis can be readily screened using assays described in the examples below.

As used herein, a therapeutic agent that inhibits or reduces one or more of, the catalytic activity and function of the proteolytically cleaved intracellular domain-containing fragments of an RPTP (i.e., RPTP inhibiting agent) refers to a composition comprised of a substance that decreases and/or suppresses the catalytic and/or functional activity of the intracellular domain-containing fragments to promote cancer cell motility, migration, dispersal, and/or metastasis. The catalytic or functional activity of the proteolytically cleaved intracellular domain-containing fragments of the RPTP can be suppressed, inhibited, and/or blocked in several ways including: direct inhibition of the activity of the intracellular domain-containing fragments (e.g., by using neutralizing antibodies, small molecules or peptidomimetics, dominant negative polypeptides); inhibition of genes that express the RPTP (e.g., by blocking the expression or activity of the genes and/or proteins); activation of genes and/or proteins that inhibit one or more of, the catalytic activity and function of the intracellular domain-containing fragments (e.g., by increasing the expression or activity of the genes and/or proteins); inhibition of genes and/or proteins that are downstream mediators of the proteolytically cleaved intracellular domain-containing fragments (e.g., by blocking the expression and/or activity of the mediator genes and/or proteins); introduction of genes and/or proteins that negatively regulate one or more of, catalytic activity and function of the proteolytically cleaved intracellular domain-containing fragments (e.g., by using recombinant gene expression vectors, recombinant viral vectors or recombinant polypeptides); or gene replacement with, for instance, a hypomorphic mutant of the RPTP (e.g., by homologous recombination, overexpression using recombinant gene expression or viral vectors, or mutagenesis).

The wedged shaped domain (i.e., wedge domain) of the juxtamembrane portion of an intracellular domain-containing fragments can potentially engage in homophilic binding and that inhibition of this binding can inhibit or reduce catalytic or functional activity of the intracellular domain-containing fragments. Compounds or compound compositions that interferes with this homophilic binding are expected to interfere with the one or more of, the catalytic activity and function of the proteolytically cleaved intracellular domain-containing fragments. It is shown in the examples below that therapeutic agents, such as peptide inhibitors, which target intracellular domain-containing fragments and particularly the wedge domain, are potent inhibitors of cancer cell motility, migration, dispersal, and/or metastasis.

In certain embodiments, the therapeutic agent can bind to, complex with, and/or act as a steric or competitive inhibitor of the proteolytically cleaved intracellular domain-containing fragments of the RPTP. Competitive inhibitors refer to proteins or polypeptides that inhibit the bioactivity of the endogenous, wild type form of the protein (i.e., RPTP (e.g., PTPμ)). As a result, a competitive inhibitor of the RPTP promotes the normal functions of RPTP in inhibiting cancer cell migration.

In one example, a competitive inhibitor of the RPTP can be a dominant negative mutant of the RPTP, which when proteolytically cleaved generates an intracellular domain-containing fragments that does not promote cancer cell motility, migration, dispersal, and/or metastasis. Examples of dominant negative mutants of the RPTP can be readily designed and screened using cell migration assays described in the Examples below as well as in *J Biol Chem* 2006; 281: 16482-92.

In one embodiment, the therapeutic agent that inhibits one or more of, the catalytic activity and function of the intracellular domain-containing fragments of the RPTP, can include a peptide or small molecule that binds to and/or complexes with the proteolytically cleaved intracellular domain-containing fragments of the RPTP to inhibit one or more of, the catalytic activity and function. In one example, the therapeutic agent can bind to or complexes with the RPTP type IIb (e.g., PTPμ). As the wedge domain can potentially engage in homophilic binding, the agent can be a peptide that has an amino acid sequence that is substantially homologous to about 10 to about 30 consecutive amino acids of a portion of the intracellular domain-containing fragments that includes the wedge domain. By substantially homologous, it is meant the peptide has at least about 80%, about 90%, about 95%, about 96%, about 97%, about 98%, about 99% or about 100% sequence identity with a portion of the amino acid sequence of the wedge domain. In one embodiment, the peptide can be substantially homologous to about 10 to about 20 consecutive amino acids of SEQ ID NO: 2. An example of a peptide that can specifically bind to SEQ ID NO: 2 can have an amino acid sequence of SEQ ID NO: 3.

One or more of, the peptides and proteins described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to flavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or non-conservative (e.g., D-amino acids) in the polypeptide sequence where such changes do not substantially alter the overall competitive inhibitor ability of the polypeptide.

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the RPTP (without being restricted to the present examples).

The peptides and/or proteins of this application may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the peptides and/or proteins may be done by affinity methods, ion exchange chromatography, size exclusion chromatography, hydrophobicity or other purification technique typically used for protein purification. The purification step can be performed under non-denaturating conditions. On the other hand, if a denaturing step is required, the protein may be renatured using techniques known in the art.

The peptides and/or proteins described herein can also be in the form of a conjugate protein or drug delivery construct having at least a transport subdomain(s) or moiety(ies) (i.e., transport moieties). The transport moieties can facilitate uptake of the peptides and/or proteins into a mammalian (i.e., human or animal) tissue or cancer cell. The transport moieties can be covalently linked to a peptides and/or proteins. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the polypeptide.

The transport moieties can be repeated more than once in the peptides and/or proteins. The repetition of a transport moiety may affect (e.g., increase) the uptake of the peptides and/or proteins by a desired cancer cell. The transport moiety may also be located either at the amino-terminal region of an active agent or at its carboxy-terminal region or at both regions.

In one embodiment, the transport moiety can include at least one transport peptide sequence that allows the peptides and/or proteins to penetrate into the cell by a receptor-independent mechanism. In one example the inhibitory peptide is a synthetic peptide that contains SEQ ID NO: 3 and a cell-penetrating motif having the SEQ ID NO: 4. SEQ ID NO: 4 is a Tat-mediated protein delivery sequence, polyargine sequences and antennapedia. An inhibitory peptide comprising SEQ ID NO: 3 and SEQ ID NO: 4 has an amino acid sequence of SEQ ID NO: 5.

Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a His-tidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the peptide agents described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In another example, the agent, which inhibits function of the intracellular domain-containing fragments of the RPTP described in this application, can include an agent that reduces or inhibits RPTP expression in the cancer cells to inhibit cancer cell motility, migration, dispersal, and/or metastasis. "Expression", means the overall flow of information from a gene to produce a gene product (typically a protein, optionally post-translationally modified or a functional/structural RNA).

In another embodiment, the agent can include an RNAi construct that inhibits or reduces expression of the RPTP in the cancer cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, Nucleic Acids Res, 25:776-780; J Mol Recog 7:89-98; Nucleic Acids Res 23:2661-2668; Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Proc Natl Acad Sci USA, 98:9742-9747; EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev,* 2002, 16:948-58; Nature, 2002, 418:38-9; *RNA,* 2002, 8:842-50; and *Proc Natl Acad Sci,* 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the RPTP expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in E coli strain DH5α cells. After positive clones are selected, plasmid can be transfected into 293T cells by calcium precipitation. The viral supernatant collected containing shRNA can then be used to infect mammalian cells in order to down regulate the RPTP.

In another embodiment, the therapeutic agent can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., RPTP).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In another embodiment, the therapeutic agent can include a substantially full-length RPTP that is substantially homologous to the RPTP that is proteolytically cleaved in the cancer cell being treated. Over-expression of a substantially full-length RPTP in cancer cells expressing the RPTP can modulate (e.g., inhibit) cancer cell motility, migration, dispersal, and/or metastases. By substantially full-length RPTP it is meant that RPTP has at least about 80%, about 90%, about 95%, about 96%, about 97%, about 98%, about 99% or about 100% sequence identity with full-length RPTP. Gene therapy methods of transfecting cancer cells with vectors encoding RPTP can be readily employed to express and/or over-express the RPTP.

In some embodiments, the agents can be provided in a pharmaceutical composition. The pharmaceutical compositions can include a pharmaceutically effective amount of a RPTP inhibiting agents described above and a pharmaceutically acceptable diluent or carrier.

The term "pharmaceutically acceptable carrier", "diluents", "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as glioblastoma multiforme. It is also to be understood herein that a "pharmaceutically effective amount" may be interpreted as an amount giving a desired therapeutic effect, either taken into one dose or in a dosage or route or taken alone or in combination with other therapeutic agents. A "pharmaceutically effective amount" may be understood as an amount of RPTP inhibiting agent to reduce the activity of proteolytically cleaved intracellular domain-containing fragments of the RPTP, to reduce the expression of RPTP, to inhibit cancer cell motility, migration, dispersal, and/or metastasis.

Determination of a therapeutically effective amount is within the capability of those skilled in the art. The exact formulation, route of administration and dosage can be chosen by the individual physician in view of the patient's condition.

Pharmaceutical compositions described herein can be administered in a suitable pharmaceutical carrier by one of several routes, which include direct injection, and topical application. Formulations of the compositions will vary according to the route of administration selected (e.g., solution or emulsion).

In certain embodiments, the agent can be delivered to cancer cells by site-specific means. Cell-type-specific delivery can be provided by coupling or conjugating a therapeutic agent to a targeting moiety, for example, one that selectively binds to cancer cells expressing the RPTP that is proteolytically cleaved to form an intracellular domain-containing fragments and an extracellular fragment. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In one embodiment, the targeting moiety that is coupled or conjugated to the therapeutic agent can include a peptide or targeting peptide that binds to and/or complexes with the proteolytically cleaved extracellular fragment of the RPTP. The targeting peptide can have an amino acid sequence that is substantially homologous to about 10 to about 50 consecutive amino acids of a homophilic binding portion or domain of the proteleolytically cleaved extracellular fragment of the RPTP. By substantially homologous, it is meant the targeting peptide has at least about 80%, about 90%, about 95%, about 96%, about 97%, about 98%, about 99% or about 100% sequence identity with a portion of the amino acid sequence of the homophilic binding portion of the proteleolytically cleaved extracellular fragment of the RPTP.

In one embodiment, the homophilic binding portion of the RPTP can include, for example, an Ig domain of the RPTP. In another example, where the RPTP is PTPμ, the homophilic binding portion can include the Ig binding domain and the MAM domain.

In another example, the targeting peptide can have an amino acid sequence that is substantially homologous to about 10 to about 50 consecutive amino acids of the Ig binding domain and/or MAM domain of PTPμ (e.g., SEQ ID NO: 1) and readily cross the blood brain barrier when systemically administered to a subject. The development of the PTPμ targeting peptides can be based on a large body of structural and functional data. The sites required for PTPμ-mediated homophilic adhesion have been well characterized. In addition, the crystal structure of PTPμ can provide information regarding which regions of each functional domain are likely to be exposed to the outside environment and therefore available for homophilic binding and thus detection by a peptide probe.

In yet another example, the proteolytically cleaved extracellular fragment of PTPμ can include an amino acid sequence of SEQ ID NO: 18 containing the MAM, Ig and first two FNIII repeats, the Ig and MAM binding region can comprise the amino acid sequence of SEQ ID NO: 19, and targeting peptide can have an amino acid sequence that is substantially homologous to about 10 to about 50 consecutive amino acids of SEQ ID NO: 18 or SEQ ID NO: 19. Examples of targeting peptide that can specifically bind SEQ ID NO: 18 or SEQ ID NO: 19 can have an amino acid sequence selected from the group consisting of SEQ ID NO: 20, SEQ ID NO: 21, SEQ ID NO: 22, and SEQ ID NO: 23. Targeting peptides comprising SEQ ID NO: 20 or 21 can recognize or bind to the MAM domain; whereas targeting peptides comprising SEQ ID NO: 22 or 23 can recognize or bind to the Ig domain. Targeting peptides comprising SEQ ID NO: 20, 21, 22 or 23 can recognize or bind to the MAM, Ig domain or the FNIII repeats.

In another embodiment, the targeting peptide and therapeutic agent can be conjugated onto a nanoparticle. An example of a the structure of a nanoparticle peptide targeted conjugate is illustrated in FIGS. 18(A-B), which show respectively the structure of a targeted nanoparticle conjugate containing a targeting peptide, the therapeutic peptide, and a fluorophore (or gadolinium) imaging agent and the structure of the targeted nanoparticle conjugate containing a targeting peptide, the therapeutic peptide and an MRI contrast imaging agent. Nanoparticles are a new class of drug carriers with precisely defined nanosize (2-5 nm). These carriers have compact molecular morphology and high surface functionalities for effective conjugation of targeted agents, therapeutic agents and imaging agents. In one example, the nanoparticle can have a size (e.g., about 3 nm) that allows effective transport and distribution of the targeted delivery systems in solid tumors.

The targeting peptide can be conjugated to the surface of the nanoparticle via, for example, a PEG spacer (e.g., 1,000 Da) to a functional group pre-conjugated to the nanoparticle. The PEG spacer is designed to reduce the steric hindrance of the drug carrier and to achieve effective specific binding to the target. The therapeutic peptide can be conjugated to the nanoparticle via, for example, a disulfide spacer. The disulfide spacer can be designed to release the therapeutic peptide in cytoplasm, which has a high concentration of reductive glutathione (e.g., about 3 mM). The disulfide spacer can be readily reduced by cytoplasmic glutathione to release the therapeutic peptide inside cancer cells.

In some embodiments, the nanoparticle comprising the therapeutic peptide and targeting peptide can be directly or indirectly labeled with a detectable moiety or imaging agent. The role of a detectable moiety is to facilitate the detection step of a nanoparticle by allowing visualization of the complex formed by binding of the targeting peptide to the proteolytically cleaved extracellular fragment of the RPTP of the cancer cell. The detectable moiety can be selected such that it generates a signal, which can be measured and whose intensity is related (preferably proportional) to the amount of the nanoparticle bound to the tissue being treated. Methods for labeling biological molecules, such as polypeptides and antibodies are well-known in the art (see for example, *Methods in Enzymol.*, 1974, Vol. 34, Academic Press: New York, N.Y.; and, *Anal. Biochem.*, 1988, 171: 1-32).

Distinct detectable moieties can be used to practice different embodiments. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some embodiments, the nanoparticles described herein may be used in conjunction with non-invasive imaging (e.g., neuroimaging) techniques for in vivo imaging of the molecular probe, such as magnetic resonance spectroscopy (MRS) or imaging (MRI), or gamma imaging, such as positron emission tomography (PET) or single-photon emission computed tomography (SPECT). The term "in vivo imaging" refers to a method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

By way of example, a fluorophore, or a magnetic resonance imaging (MRI) contrast agent, (e.g., Gd-DOTA), can be directly conjugated to the nanoparticle to allow the visualization of the delivery process.

In one embodiment, the agent described herein can be administered to a cancer cell, e.g., glioblastoma multiforme cell, prostate cancer, lung cancer, melanoma, or tumor-derived endothelial cell of a subject by contacting the cell of the subject with a pharmaceutical composition described above. In one aspect, a pharmaceutical composition can be administered directly to the cell by direct injection. Alternatively, the pharmaceutical composition can be administered to the subject systematically by parenteral administration, e.g., intravenous administration).

In a further example, the therapeutic agent can be used in combination and adjunctive therapies for inhibiting cancer cell proliferation, growth, and motility. The phrase "combination therapy" embraces the administration of a therapeutic agent, which inhibits the one or more of, the catalytic activity and function of the proteolytically cleaved intracellular domain-containing fragments of the RPTP, and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of this application.

A combination therapy is intended to embrace administration of these therapeutic agents in a sequential manner, that is, wherein different therapeutic agents are administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments the therapeutic agent, which inhibits the one or more of, the catalytic activity and function of the proteolytically cleaved intracellular domain-containing fragments of the RPTP, can be administered in combination at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Another embodiment relates to a method of screening agents that inhibit one or more of, the catalytic activity and function of the proteolytically cleaved intracellular domain-containing fragments of the RPTP. The method includes: administering a therapeutic agent to a cancer cell that includes proteolytically cleaved intracellular domain-containing fragments of the RPTP; and detecting the motility, migration, and/or dispersal of the cell. Therapeutic agents that decrease the cancer cell motility, migration, and/or dispersal compared to control are indicative of an effective agent.

Embodiments can be used with respect to an agent that affects (e.g., reduces, inhibits, eliminates, or ameliorates) one or more of, the catalytic activity and function of the intracellular domain-containing fragments. Agents screened can include nucleic acids, peptides, proteins, antibodies, antisense RNAs, RNAi constructs (including siRNAs), DNA enzymes, ribozymes, morpholino constructs, chemical compounds, and small organic molecules. Agents may be screened individually, in combination, or as a library of agents. Agents to be screened in the described methods can be produced, for example, by bacteria, yeast or other organisms (e.g., natural products), produced chemically (e.g., small molecules, including peptidomimetics), or produced recombinantly. In one example, the test agent is a small organic molecule having a molecular weight of less than about 2,000 daltons.

In many drug screening programs, which test libraries of compounds and natural extracts, high throughput assays are desirable in order to maximize the number of compounds surveyed in a given period of time. Assays described herein, which are performed in cell-free systems may be developed with purified or semi-purified proteins or with lysates, are often preferred as "primary" screens in that they can be generated to permit rapid development and relatively easy detection of an alteration in a molecular target which is mediated by a test agent. Moreover, the effects of cellular toxicity and/or bioavailability of the test agents can be generally ignored in such a system, the assay instead being focused primarily on the effect of the agent.

The efficacy of the therapeutic agent can be assessed by generating dose response curves from data obtained using various concentrations of the test agent. Moreover, a control assay can also be performed to provide a baseline for comparison. Such candidates can be further tested for efficacy in inhibiting chemotaxis of cancer cells in vitro, spreading, invasion, or migration of cancer cells in vitro, for efficacy in tumor dispersal, or spreading in vitro or in vivo. For example, the efficacy of the agent can be tested in vivo in animal cancer models.

Cell-based assays may be performed as either a primary screen, or as a secondary screen to confirm the activity of agents identified in a cell free screen, such as an in silico screen. Such cell based assays can employ a cell-type expressing proteolytically cleaved intracellular domain-containing fragments of the RPTP. Exemplary cell types include cancer cell lines, primary tumor xenografts, and glioma cells. Cells in culture are contacted with one or more agents, and the ability of the one or more agents to inhibit cell migration/invasion is measured. Agents that inhibit cell migration/invasion are candidate agents for use in the subject methods of inhibiting tumor progression. For example, the identified compounds can be tested in cancer models known in the art.

The following examples are included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

EXAMPLE 1

In this example, it is shown the loss of PTPµ protein expression in highly dispersive human glioblastomas, whereas less dispersive tumors and the human glioma cell line U-87 MG expresses PTPµ. shRNA-mediated knockdown of PTPµ protein in U-87 MG cells induces a morphological change, migration, and dispersal in scratch wound and adult rat brain slice assays. Furthermore, we used intracranial injection of the U-87 MG cells in an in vivo mouse xenograft model to demonstrate that loss of PTPµ induced a morphological change and tumor cell heterogeneity in the U-87 MG cells in vivo. These data show that loss of PTPµ in human glioblastomas contributes to glial tumor cell migration and dispersal.

Materials and Methods

Sample Isolation

Human primary intra-parenchymal brain tumor tissue was obtained from surgical resections. After the neuropathologists made an intraoperative diagnosis of glioma and obtained all the tissue necessary for diagnosis, remaining tissue was cryopreserved for future studies. Tissue from patients undergoing cortical resections for intractable epilepsy was collected and cryopreserved for use as non-tumor "normal" tissue. The U-87 MG and LN-229 human glioma cell lines were obtained from the American Type Culture Collection (ATCC, Manassas, Va.). U-373 MG glioma cells were obtained from Wayne State University, Detroit, Mich. LN-229 and U-87 MG cells were maintained in DMEM (Invitrogen, Carlsbad, Calif.) supplemented with 10% fetal bovine serum (HyClone, Logan, Utah) at 37° C., 5% CO2. U-373 MG cells were maintained in RPMI (HyClone) supplemented with 10% fetal bovine serum at 37° C., 5% CO2. Cell lysates were prepared from cell cultures grown to confluence. Normal rat astrocytes were prepared as described previously (*Dev Neurosci.* 2003;25:207-216).

Immunoblotting

Normal and tumor tissue lysates were prepared by adding 10 volumes of lysis buffer to tissue samples that had been frozen at the time of surgical resection. The lysis buffer contained 20 mM Tris-HCl (pH 7.0), 0.5% Triton X-100, 1 mM phenylmethylsulfonyl fluoride, 3 mM benzamidine, 5 µg/ml aprotinin, 5 µg/ml leupeptin, 1 µg/ml pepstatin A, 2 mM sodium orthovanadate, 2 mM EGTA, 5 mM EDTA, 30 mM sodium fluoride, and 40 mM beta-glycerol phosphate. The tissue was disrupted using a 2 ml frosted dounce homogenizer, incubated on ice for 30 minutes, and then sonicated and centrifuged at 3000 rpm for 3 minutes. The supernatant was collected, and the protein concentration was determined using a bicinchoninic acid (BCA) protein assay (Pierce, Rockford, Ill.). 2× SDS sample buffer was added to the lysates. The lysates were then incubated at 95° C. for 5 minutes. 30 µg of protein was loaded per lane on an SDS-PAGE gel. Lysates from glioma cell lines and cultured astrocytes were prepared similarly. PTPµ expression was analyzed by immunoblot using the intracellular antibodies SK-15 and SK-18 as described previously (*J Cell Biol.* 1993;122:961-972; *Mol Cell Biochem.* 1993;127-128:131-141). An antibody against actin (JLA20) was obtained from the Developmental Studies Hybridoma Bank (University of Iowa, Iowa City, Iowa). Antibodies recognizing N-cadherin and vinculin were from BD Biosciences (San Jose, Calif.) and Sigma-Aldrich (St. Louis, Mo.), respectively. Densitometry analyses were performed using either the Quantity One imaging software of the Fluor-S Max MultiImager system (Bio-Rad, Hercules, Calif.) or ImageJ software (Rasband W S, *ImageJ.* 1997-2008, U.S. National Institutes of Health: Bethesda, Md., USA). PTPµ densitometry values were calculated by adding the densities of the full-length and cleaved bands.

PTPµ Knockdown

Lentiviral shRNA constructs V2LHS_171008 (shRNA #1) and V2LHS_171013 (shRNA #2) targeting human PTPµ mRNA were purchased from Open Biosystems (Huntsville, Ala.). A control lentiviral shRNA construct was a gift from Drs. E. Johnson and R. Keri. VSV-G-pseudotyped lentiviral particles were generated by triple transfection of shRNA constructs with the packaging plasmids pCMVΔR8.91 and pMD.G into 293T cells using Lipofectamine 2000 (Invitrogen) according to a previously described protocol (*J Virol.* 1998;72:8463-8471). The particles were concentrated by ultracentrifugation and used to infect cells in the presence of 6 µg/ml of polybrene. Cells were harvested or assayed at three days post-infection. Knockdown of PTPµ by lentiviral shRNA was verified by immunoblotting with antibodies to PTPµ. The infection efficiency with lentiviral shRNA constructs containing a green fluorescent protein (GFP) reporter was visualized by fluorescence microscopy.

RNA Extraction and RT-PCR

RNA was isolated from U-87 MG cells expressing either control or PTPµ shRNA using Trizol according to the manufacturer's protocol (Invitrogen). RNA concentrations from each condition were determined by reading the absorbance at 260 nm using a spectrophotometer and were normalized. cDNA was prepared from 1 µg of RNA using a ThermoScript RT-PCR system from Invitrogen. PCR was performed using the following parameters: 93° C. for 30 seconds, 58° C. for 30 seconds, and 72° C. for 30 seconds for 35 cycles followed by a 5 minute extension at 72° C. Primers designed against the 5' end of the mRNA of PTPµ-like subfamily members were as follows:

```
PTPµ forward
                                          (SEQ ID NO: 6)
(GGGAGGAGGACCCAGGAC), PTPµ reverse
                                          (SEQ ID NO: 7)
(TGTACGTGTTGGGTCTCCAG), PTPρ forward
                                          (SEQ ID NO: 8)
(CCCTCAGCCTGCTCCTGA),
```

```
PTPρ reverse
                       (SEQ ID NO: 9)
(CCACCATTCACCTTCACGTA),

PTPκ forward
                       (SEQ ID NO: 10)
(AAACTCGGCATGGATACGAC),

PTPκ reverse
                       (SEQ ID NO: 11)
(GGCATCTCGGGTGGTAGATA),

PCP-2 forward
                       (SEQ ID NO: 12)
(CAGGCCCAGTACGATGACTT),
and PCP-2 reverse
                       (SEQ ID NO: 13)
(AGCTGAACTGCACACAGTGG).
```

Scratch Wound Assay

U-87 MG cells were infected with control or PTPµ shRNA lentivirus. After three days, confluent monolayers of cells were scratched with a 20 µl pipette tip to induce a wound. The wounded edges were imaged using a Nikon (Tokyo, Japan) TE200 inverted microscope and Spot RT digital camera and image acquisition software (Diagnostic Instruments, Inc., Sterling Heights, Mich.) Images were collected with a 10× objective 0, 6, 24, and 48 hours after wounding. Images were quantitated using MetaMorph software (Molecular Devices, Downingtown, Pa.) by measuring the width of the wound at each time point. The difference between the width of the wound at the zero time point and the time point being analyzed was divided by two. This value reflects the distance migrated by the leading edge of one side of the wound during a given time interval. Replicates were averaged and plotted using Microsoft Excel. Error bars indicate standard error. Data were analyzed for statistical significance using an unpaired student's t-test. Rac1 inhibition studies were performed using a Rac1-specific inhibitor from Calbiochem (Gibbstown, N.J.) (*J Biol Chem.* 2005;280:37516-37525; *Proc Natl Acad Sci USA.* 2004;101:7618-7623). For morphological studies, the inhibitor was dissolved in water and added at a final concentration of 100 µM just prior to scratching the cells. Cells were analyzed after 6 hours. For migration studies, the inhibitor was dissolved in water and added at a final concentration of 50 µM just prior to scratching the cells. Cells were analyzed after 24 hours.

Cell Cycle Analysis

U-87 MG cells were infected with control or PTPµ shRNA lentivirus and serum arrested with basal media at 24 hours post-infection. Cells were either growth-arrested in serum free media for 48 hours or stimulated after 24 hours with complete medium containing 10% serum for an additional 24 hours. Propidium iodide labeling of cells for cell cycle analysis by flow cytometry has been described previously (*Cytometry.* 1992;13:48-59). Briefly, cells were trypsinized, washed three times with phosphate-buffered saline (PBS) and fixed in ice-cold methanol. Fixed cells were washed twice with PBS, treated with RNase, and labeled with 50 µg/ml propidium iodide. Cell cycle analysis was performed in two separate experiments using a Coulter EPICS XL-MCL flow cytometer (Beckman Coulter Inc., Fullerton, Calif.) and analyzed using ModFit LT (Verity Software House, Topsham, Me.). Replicates were averaged and plotted using Microsoft Excel. Error bars indicate standard error.

Preparation of Brain Slices

Organotypic brain slice cultures were prepared according to previously described protocols (*Dev Neurosci.* 2003;25: 207-216; *Nat Protoc.* 2006;1:1165-1171) with some modifications. Adult female Sprague-Dawley rats aged 10-12 weeks were used for the preparation of brain slices into which human tumor cells were injected. Animals were purchased from Harlan Laboratories (Indianapolis, Ind.). Whole brains were dissected, embedded in 2% agarose in PBS, and sliced into 300 µm-thick coronal sections using a vibratome (Leica Microsystems, Inc., Bannockburn, Ill.). Slices were collected in cold calcium/magnesium-free phosphate buffer (CMF) supplemented with 0.5% glucose and placed on membrane culture inserts (Millipore, Billerica, Mass.) of 6-well dishes. Slices were cultured in media containing 50% MEM, 25% horse serum, and 25% CMF supplemented with 0.5% glucose, 2 mM L-glutamine, and antibiotic/antimycotic solution (Invitrogen) at 37° C., 5% $CO_2$.

Brain Slice Assay

U-87 MG cells were injected into prepared brain slices with modifications to a previously described protocol (*Neurosurgery.* 2003;52:187-196). U-87 MG cells were infected with lentiviral shRNA constructs encoding control or PTPµ shRNA containing a GFP reporter. Cells were trypsinized at three days post-infection and resuspended in DMEM containing 2 mg/ml Matrigel (BD Biosciences) at a concentration of 105 cells/µl. Cells were injected into the cortex of 1 day-old rat brain slices by creating a small indentation with a 2 µl micropipettor and implanting 0.5 µl of the cell suspension. Slices were incubated for 48 hours and then fixed in 4% paraformaldehyde overnight. After washing in PBS, the slices were mounted on slides and then viewed under a fluorescence-equipped microscope to evaluate cell migration and dispersal into the brain tissue via GFP fluorescence. Images were taken with a 10× objective using a Leica DMI 6000 B automated inverted microscope (Leica Microsystems GmbH, Wetzlar, Germany) attached to a Retiga EXi camera (QImaging, Surrey, BC, Canada).

We developed a quantitative method for determining the migration and dispersal of injected tumor cells in brain slices using MetaMorph software (Molecular Devices, Downingtown, Pa.). Briefly, the area of the injection site was excluded, and the image was deconvolved to reduce flaring. Next, the area near the injection site was thresholded using parameters that highlighted only cells that had dispersed away from the injection site. Five regions of 200×200 µm were selected near the injection site. The number of highlighted pixels in each region was determined and used to calculate the thresholded area in square µm. Control and test brain slices were analyzed using identical parameters. The thresholded areas for each image were averaged for each cell type and plotted using Microsoft Excel. Studies were repeated in three separate experiments with at least 11 replicates. Error bars indicate standard error. Data were analyzed for statistical significance using an unpaired student's t-test.

Intracranial Xenograft Model

Intracranial xenograft experiments were performed in accordance with an approved protocol from the Cleveland Clinic Institutional Animal Care and Use Committee. U-87 MG cells expressing either control or PTPµ shRNA were trypsinized and washed in complete medium followed by a PBS wash. $2.5 \times 10^4$ cells were resuspended in 3 µl PBS to implant intracranially into the right hemisphere of nude mice. A small animal stereotactic manipulator was used to inject the cell suspension 2 mm lateral, 0.5 mm anterior, and 3 mm inferior to bregma as a reference point. Six animals were injected for each cell type. After two weeks, animals were sacrificed. Whole brains were fixed in 10% paraformaldehyde, washed with PBS and PBS with 10% and 20% sucrose, frozen in OCT, and cryosectioned into 10 μm sections. Sections were either stained with hematoxylin and eosin or mounted in medium containing DAPI. Brightfield and fluorescent images were acquired with a 40× objective using a Leica DM 5000 B automated inverted microscope (Leica Microsystems GmbH) attached to a Retiga SRV cooled CCD camera (QImaging). Images were collected using ImagePro Plus (Media Cybernetics, Bethesda, Md.) and Turboscan Surveyor (Objective Imaging, Kansasville, Wis.) software systems. Confocal fluorescent images were acquired with a 63× objective using an upright Leica TCS-SP2 spectral laser scanning confocal microscope (Leica Microsystems GmbH) and Volocity 3D imaging software (Improvision, Inc., Lexington, Mass.).

PTPμ is Expressed in Astrocytes

Figure 1:
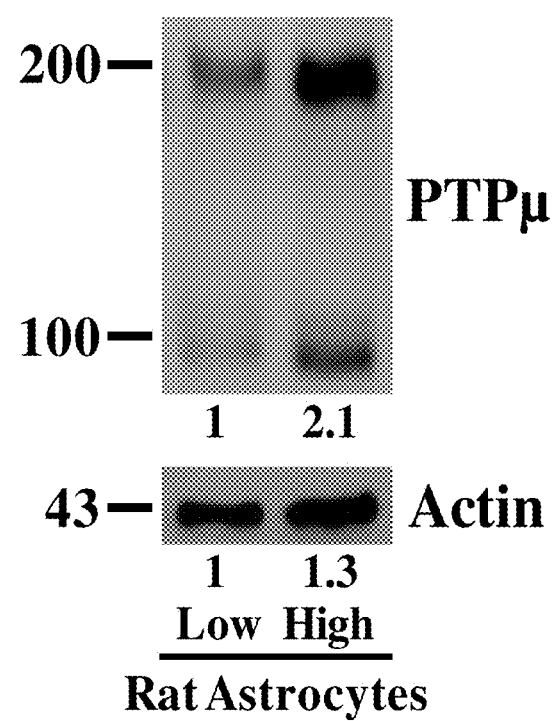
FIG. 1 illustrates an immunoblot showing PTPμ is up-regulated at high cell density in primary rat astrocytes. Lysates from rat astrocyte cells grown at low and high density were separated by SDS-PAGE and immunoblotted for PTPμ. PTPμ was expressed as a 200 kDa precursor protein that is normally proteolytically processed into two 100 kDa fragments that are tightly associated. Actin was used as a loading control. The values underneath each lane represent the fold increase of the high density sample compared to the low density sample based upon densitometry. The numbers on the left side of the immunoblot correspond to the molecular weight in kDa.

Astrocytomas resemble normal astrocytes histologically. Like many other cell types, normal astrocytes exhibit density-dependent contact inhibition of growth (*J Neurosci Res.* 2001;66:487-496). PTPμ protein expression was examined in primary astrocytes grown at low and high cell density (FIG. 1). Primary rat astrocytes express both the full-length (200 kDa) and proteolytically processed form of PTPμ (100 kDa). Cleavage of PTPμ occurs in the endoplasmic reticulum and results in two non-covalently bound, tightly-associated fragments (*J Biol Chem.* 1994;269:28472-28477). More importantly, PTPμ protein is stabilized at the plasma membrane in primary astrocytes at high cell density (FIG. 1), consistent with previous data in other cell types (*J Cell Biol.* 1995;131:251-260). Therefore, PTPμ is a good candidate to regulate density-dependent events such as contact inhibition of growth and migration.

PTPμ Expression is Reduced in Gliomas

Figure 2:
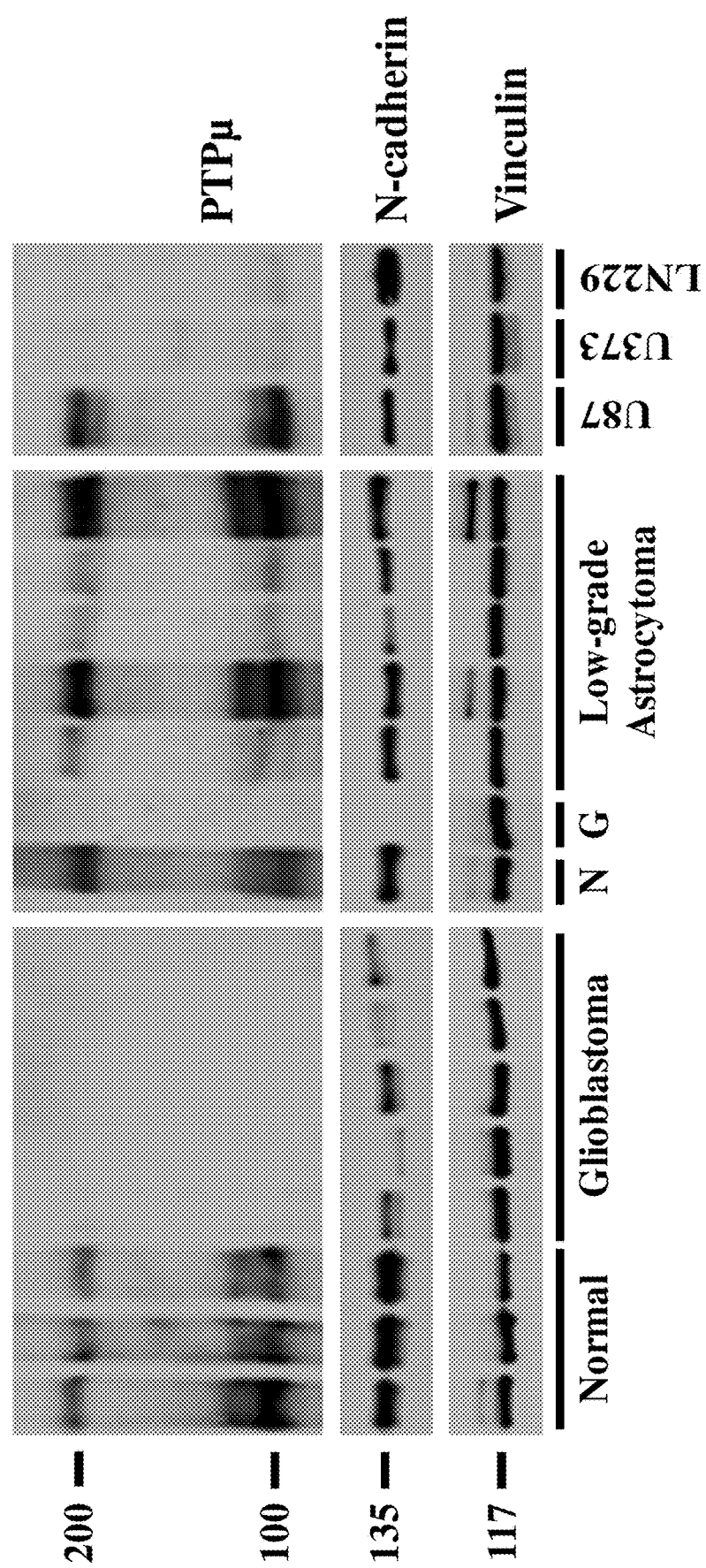
FIG. 2 illustrates an immunoblot showing PTPμ expression in brain tumor tissue and cell lines as determined by immunoblotting. PTPμ was expressed in normal brain tissue (N), low-grade astrocytomas, and U-87 MG cells. PTPμ was not expressed in primary human glioblastomas (G) or LN-229 and U-373 MG cell lines. N-cadherin expression was used as a control for the expression of another cell surface protein; vinculin expression as a control for protein loading. The numbers on the left side of the immunoblot correspond to the molecular weight in kDa.

In an effort to understand the role of PTPμ in gliomas, we examined the PTPμ protein levels among human glioma tumors compared to control tissue. PTPμ protein expression was strikingly reduced in glioblastoma. For example, five independent primary GBM samples had dramatically reduced levels of PTPμ compared to brain tissue obtained from epilepsy patients (FIG. 2). An additional five GBM samples showed loss of PTPμ expression (data not shown). In contrast to GBMs, low-grade astrocytoma samples maintained some level of PTPμ expression. Next, we assessed the expression of PTPμ protein in the commonly used human glioma cell lines U-87 MG, U-373 MG, and LN-229. U-373 MG and LN-229 cells are migratory in vitro (*Cancer Res.* 2007;67:7203-7211) and expressed very little PTPμ protein (FIG. 2). U-87 MG cells exhibit some migration in vitro but must be treated to stimulate substantial migration (*Cancer Res.* 2007;67:7203-7211). In contrast to U-373 MG and LN-229 cells, U-87 MG cells expressed significant levels of PTPμ. As a control for the expression of another cell surface adhesion molecule, N-cadherin expression was examined in these samples. Somewhat unexpectedly, glioblastoma samples exhibited a variable decrease in the level of N-cadherin expression. Vinculin expression was used as a control for protein loading among the tissue samples. Densitometry analyses of the 200 and 100 kDa bands on the immunoblots indicate that there is a complete reduction of PTPμ expression in GBMs compared to non-tumor tissue following normalization for the vinculin loading control. These results suggest that loss of PTPμ protein expression may be an important event in glioma progression.

PTPμ Regulates Cell Migration In Vitro

Because of the significant loss of PTPμ in GBM tumor samples and the dispersive nature of this tumor, we hypothesized that PTPμ suppresses cell migration. To determine whether PTPμ expression affects cell migration directly, shRNA was used to knock down PTPμ in U-87 MG cells, and the migration of these cells was analyzed in vitro using a scratch wound paradigm. U-87 MG cells were infected with lentivirus containing control shRNA or two PTPμ shRNAs targeting different mRNA sequences. Lysates of these cells at three days post-infection were analyzed for PTPμ protein levels by immunoblot and show a 4.5-fold reduction of PTPμ protein expression as determined by densitometry (FIG. 3A). RT-PCR analysis of other PTPμ-like subfamily members (PTPρ, PTPκ, and PCP-2) indicated that only PTPμ mRNA is targeted for degradation by PTPμ shRNA (FIG. 3B). In addition, these data indicate that PTPκ and PCP-2 are expressed in U-87 MG cells (FIG. 3B).

Figure 4A:
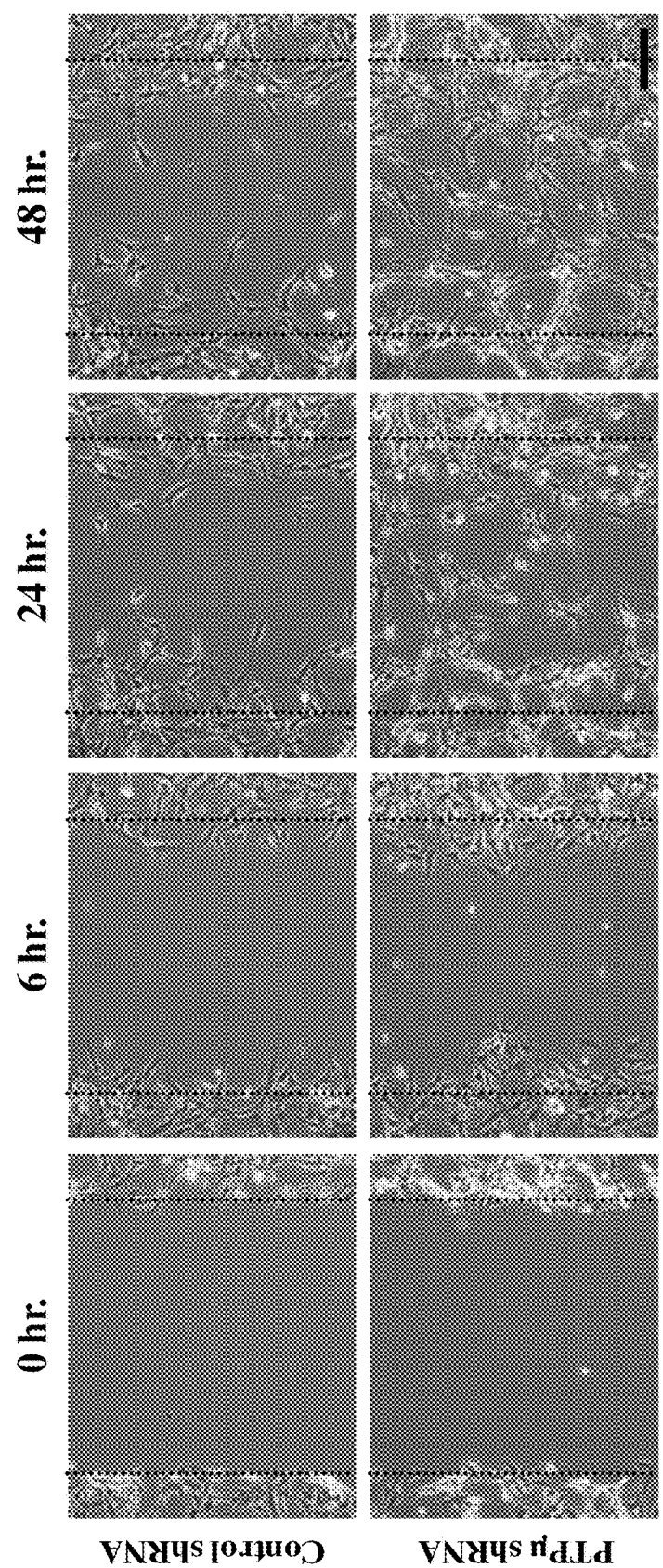
FIGS. 4(A-C) illustrate images showing knockdown of PTPμ induces migration in a scratch wound assay. Confluent monolayers of U-87 MG cells infected with either control or PTPμ shRNA were scratched with a pipette tip to create a wound. Migration of cells to fill the wound was followed over 48 hours (A). Black dashed lines mark the wound edge at 0 hours. The scale bar represents 200 μm. The distance migrated by the cells at the leading edge was quantitated and plotted (B). Asterisks represent a statistically significant difference (n=4; 24 hr., p<0.04; 48 hr., p<0.01). The central portion of the leading edge of the 6 hour panel is enlarged to show the PTPμ-dependent morphological differences (C). The scale bar represents 100 μm.

Confluent monolayers of U-87 MG cells expressing either control or PTPμ shRNA were scratched with a pipette tip to induce a wound. The wound edges were monitored over time by microscopy. Control shRNA-infected U-87 MG cells failed to migrate inward to fully close the wound, even after 48 hours. In contrast, PTPμ shRNA-infected cells migrated more rapidly and began to close the wound at 24 hours (FIG. 4A). The distance migrated by the leading edge of the wound was quantified and shows a statistically significant increase in the distance the U-87 MG cells expressing PTPμ shRNA migrated in comparison to control cells (FIG. 4B). Furthermore, the morphology of cells with PTPμ knocked down appeared to differ from control U-87 MG cells. Loss of PTPμ induced broad lamellipodial structures at the leading edge of the wound, consistent with that of a migratory cell (FIG. 4C). To ensure the morphological change induced by expression of PTPμ shRNA was not due to an off-target effect, another PTPμ shRNA was used to repeat the experiment. Both shRNA constructs induced the same lamellipodial structures (FIG. 5A).

Figure 5C:
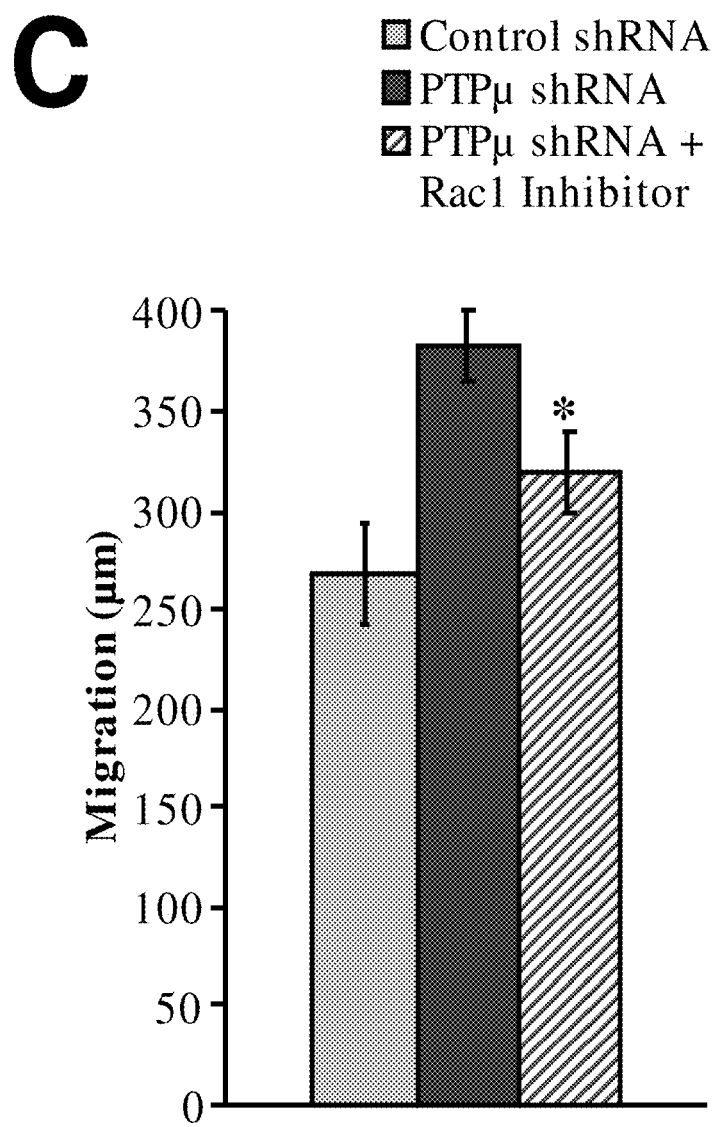
FIGS. 5(A-C) illustrate images showing Rac1 is required for the formation of lamellipodia and increased migration induced by the loss of PTPμ. U-87 MG cell cultures expressing control or two different PTPμ shRNAs were scratched and analyzed for morphological changes after 6 hours (A). Expression of both PTPμ shRNA constructs induced lamellipodia. An inhibitor of Rac1 was added at a final concentration of 100 μM just prior to scratching (B). The Rac1 inhibitor blocked the formation of PTPμ-induced lamellipodia. Scratched monolayers were analyzed to quantitate the distance migrated by the cells at the leading edge of the wound after 24 hours (C). The Rac1 inhibitor significantly reduced the migration induced by the loss of PTPμ. The asterisk represents a statistically significant difference (n≥9; p<0.04).

The formation of lamellipodia is dependent upon the activity of the Rho family GTPase Rac1 (*Cell.* 1992;70:401-410). Therefore, we hypothesized that the induction of lamellipodia by the loss of PTPμ may be Rac1-dependent. To test this, a specific inhibitor of Rac1 activity (*J Biol Chem.* 2005;280:37516-37525; *Proc Natl Acad Sci USA.* 2004;101:7618-7623) was added to the medium of U-87 MG cells expressing either control or PTPμ shRNA just prior to a scratch assay. The addition of the Rac1 inhibitor to the control U-87 MG cells had no effect on morphology (FIG. 5B). However, the Rac1 inhibitor prevented the induction of lamellipodia in the cells with reduced PTPμ expression (PTPμ shRNA #1), returning the cells to the morphology of the control cells (FIG. 5B). Additionally, the Rac1 inhibitor significantly suppressed the migration induced by the loss of PTPμ (FIG. 5C). Taken together, these data suggest that PTPμ suppresses migration of glioma cells in vitro by inhibition of Rac1 activity.

Knockdown of PTPμ in U-87 MG Cells Does Not Alter Cell Proliferation

Figure 6:
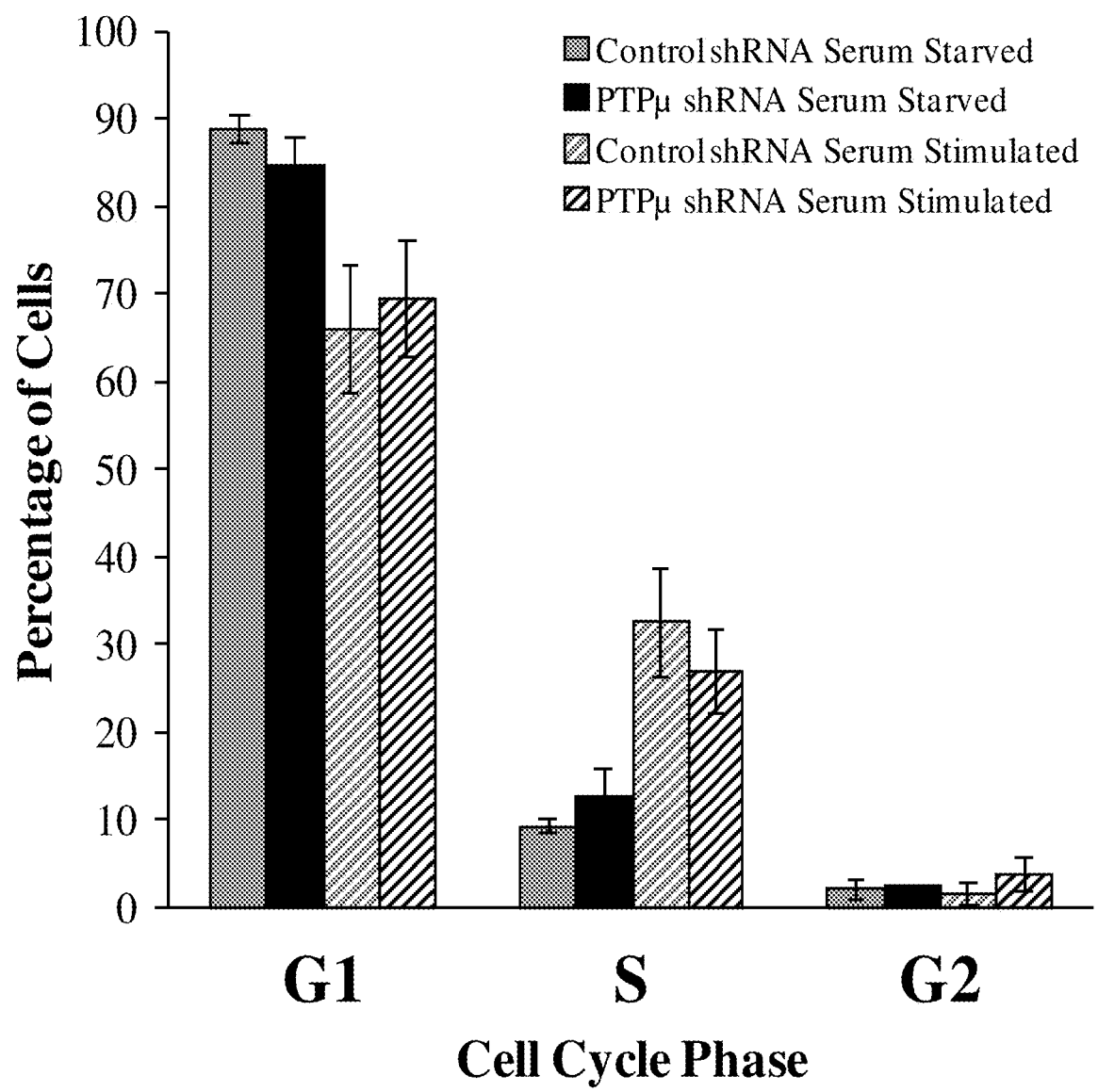
FIG. 6 illustrates a chart showing PTPμ expression does not affect cell proliferation. U-87 MG cells were infected with control or PTPμ shRNA, labeled with propidium iodide, and analyzed by flow cytometry. The percentage of cells in each phase of the cell cycle was averaged and plotted for each condition.

The results of the scratch wound assay show that PTPμ alters the migration of glial tumor cells, but the possibility remained that this effect was due to a change in proliferation. To rule out this hypothesis, the cell cycle profiles of U-87 MG cells expressing control or PTPμ shRNA were analyzed by flow cytometry. U-87 MG cells were infected with control or PTPμ shRNA and serum arrested with basal media at 24 hours post-infection. Cells either remained serum arrested for 48 hours or were stimulated after 24 hours of serum arrest with complete medium containing 10% serum for an additional 24 hours. As shown in FIG. 6, there were no significant differences in cell cycle distribution observed between either serum-arrested or serum-stimulated U-87 MG cells infected with control or PTPμ shRNA. Approximately 80% of the cells were diploid in all conditions, and the remaining aneuploid population had a similar cell cycle distribution as the diploid cells (data not shown). Therefore, PTPμ knockdown did not alter U-87 MG cell proliferation.

PTPμ Alters Migration and Dispersal in an Ex Vivo Brain Slice Assay

Figure 7C:
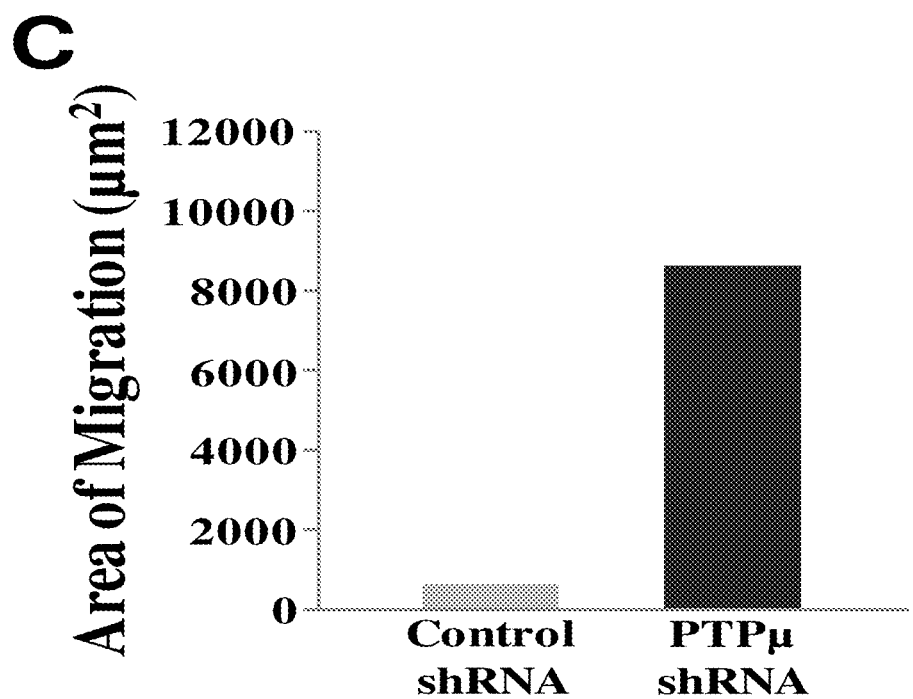
FIGS. 7(A-C) illustrate a schematic drawing and images showing knockdown of PTPμ induces U-87 MG cells to disperse in the adult rat brain slice assay. The schematic representation of the brain slice assay shows injection of glioma cells expressing GFP into the cortex of adult rat brain slices (A). Dispersive cells migrate extensively throughout the brain parenchyma, but non-dispersive cells remain at the site of injection. U-87 MG cells were infected with either control or PTPμ shRNA with a GFP reporter and injected into the cortex of adult rat brain slices (B). The dashed oval indicates the injection site margin. Control shRNA-infected U-87 MG cells remained at the injection site after 48 hours. In contrast, U-87 MG cells expressing PTPμ shRNA migrated away from the injection site over the same time interval. The scale bar represents 100 m. Data from three experiments were quantitated and plotted according to the average thresholded area of the fluorescent cells that migrated away from the injection site (C). The asterisk represents a statistically significant difference (n=11, p<0.0001).

To determine whether the absence of PTPμ in shRNA-infected U-87 MG cells influenced their migratory behavior in the complex environment of the brain, PTPμ expression was knocked down in U-87 MG glioma cells for assay in a brain slice model. A modified version of the brain slice assay for dispersal was used which more closely approximates in vivo migratory conditions (FIG. 7A). This assay allows for evaluation of dispersal and proliferation of glioma cells through the complex matrix of the adult brain, an environment that simulates glioma cell dispersal in vivo. Previous studies have characterized the behavior of primary rat astrocytes using this assay in neonatal rat brains (*Dev Neurosci.* 2003;25:207-216).

U-87 MG cells were infected with either control or PTPμ shRNA containing a GFP reporter. After three days, these cells were injected into the cortex of ex vivo adult rat brain slices. Cell migration was measured in brain slices after 48 hours. By following their migration over time using GFP fluorescence, cell movement through a 3-D matrix environment was evaluated. The assay was quantitated by measuring the average area of fluorescent cells that migrated away from the injection site in a given slice at the 48-hour time point. Control shRNA-infected U-87 MG cells were not dispersive and remained as a tight clump of cells that did not migrate into the adult brain tissue of the slice (FIG. 7B, left panel). Knockdown of PTPμ by shRNA, however, induced a significant dispersal of cells away from the injection site (FIG. 7B, right panel and 7C). Migration of these cells occurred in several focal planes of the brain tissue, suggesting dispersal throughout the three-dimensional architecture of the brain slice. These results suggest that loss of PTPμ protein expression correlates with increased migration and dispersal of the glioma cells.

Loss of PTPμ Alters Cell Morphology In Vivo

We observed a change in the morphology and dispersive phenotype of U-87 MG cells upon the loss of PTPμ in vitro and in a three-dimensional assay. Therefore, we hypothesized that these changes would be recapitulated in vivo using an intracranial mouse xenograft model. U-87 MG cells expressing control or PTPμ shRNA were intracranially implanted into nude mice to allow tumors to form. After two weeks, whole brains were sectioned to analyze the morphology of the two tumor groups. Both hematoxylin and eosin staining and GFP-labeling of the tumor cells indicate a marked difference in the morphology of the tumors in each group.

Figure 8:
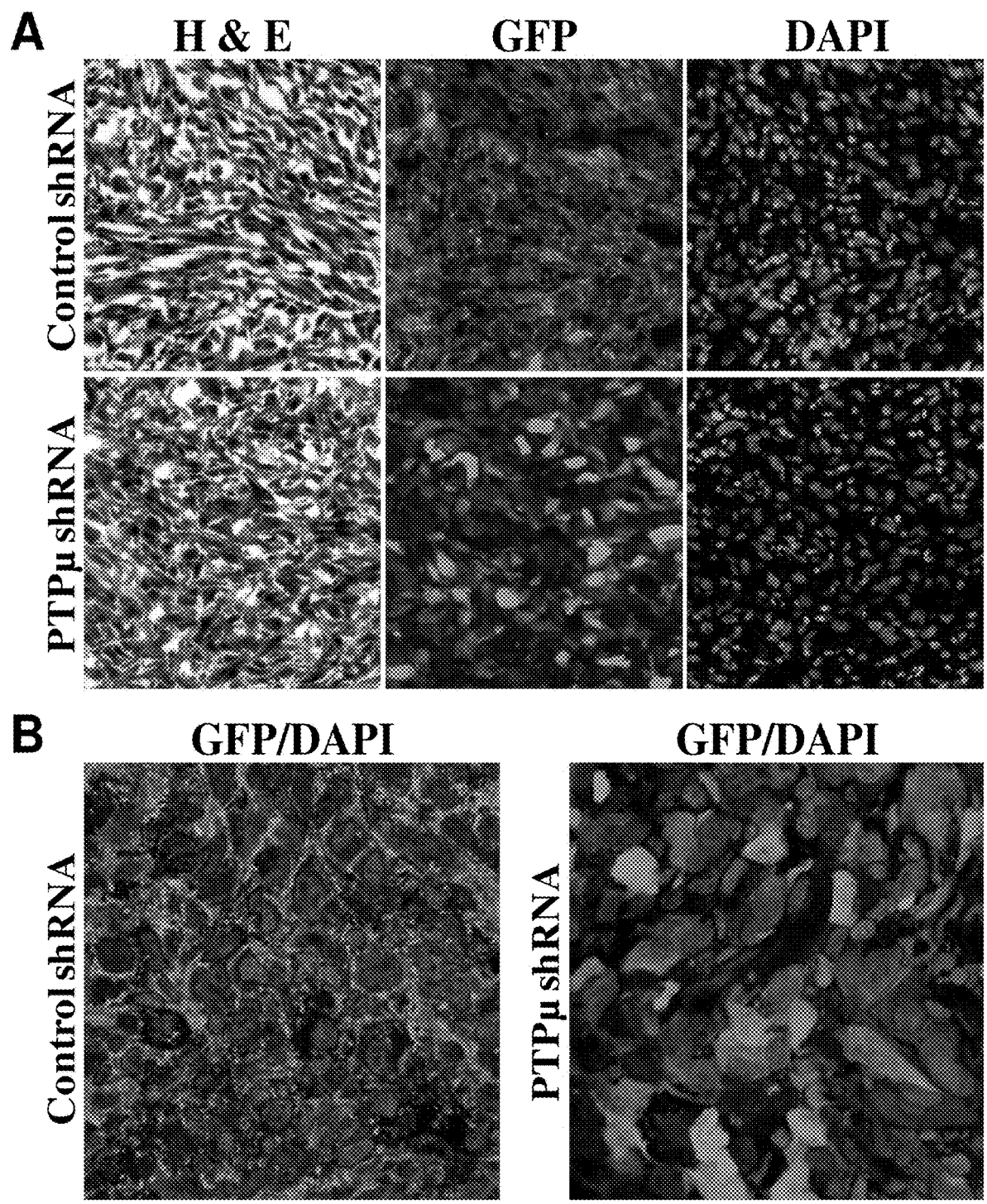
FIG. 8 illustrates images showing loss of PTPμ affects tumor morphology in vivo. Mouse xenografts of U-87 MG cells infected with control or PTPμ shRNA lentivirus were cryosectioned and analyzed for morphology. 40× images of hematoxylin and eosin (H & E) staining, GFP-labeling of tumor cells, and DAPI staining of nuclei are shown (A). Confocal 63× images of GFP-labeling and DAPI staining are merged together for both control and PTPμ shRNA-expressing U87-MG xenografts (B). Loss of PTPμ induced heterogeneity in the size and shape of the cells in the xenograft.

U-87 cells expressing control shRNA formed tightly packed tumors of cells that appear to retain cell-cell adhesion (FIG. 8A, 8B). In contrast, the tumors in which PTPμ expression was decreased by shRNA were composed of a loose mass of cells that were heterogeneous in size and shape (FIG. 8A, 8B). These changes are consistent with the pleomorphism and heterogeneity seen in infiltrative high-grade glioma tumors and support our data that the loss of PTPμ is an important molecular change in glioblastomas. Taken together, our results show that PTPμ may play an important role in contact-dependent signaling to negatively regulate migration of glial cells and that the loss of PTPμ protein expression may be advantageous to glioblastoma formation during the migration and dispersal process.

EXAMPLE 2

It is shown in this example that overexpression of full-length PTPμ in glioblastoma cells suppresses cell migration and growth factor-independent cell survival. In addition, we show that PTPμ downregulation in glioblastoma is the result of sequential cleavage of full-length PTPμ protein to generate the intracellular domain-containing fragments PΔE and inctracellular domain (ICD). It was found that the intracellular domain-containing fragments of PTPμ are present in human glioblastoma samples and glioblastoma xenograft flank tumors. Surprisingly, shRNA-mediated downregulation of PTPμ fragments decreases cell migration and growth factor-independent survival in glioblastoma cells. Furthermore, peptide inhibition of the function of PTPμ fragments inhibits cell migration. These data show that proteolytic cleavage of full-length PTPμ generates PTPμ fragments that regulate cell migration and growth factor-independent survival in glioblastoma. These PTPμ fragments can be targeted to develop novel therapeutic agents for glioblastoma patients.

Materials and Methods

Cell Lines

The human GBM cell lines U-87 MG and LN-229 were obtained from the American Type Culture Collection (ATCC, Manassas, Va).

Lentiviral Transduction

A human full-length PTPμ cDNA construct in pMT2 has been described (FEBS Lett 1991; 290: 123-30). Full-length PTPμ was ligated into the lentiviral expression vector pCDH-MCS2 (System Biosciences, Mountain View, Calif.). A full-length PTPμ-green fluorescent protein (GFP) fusion construct has been described (J Biol Chem 2002; 277: 11165-73). The PTPμ-GFP cassette was subcloned into pCDH-MCS2. An intracellular PTPμ-GFP fusion construct corresponding to PTPμ ICD has been described.

Immunoblotting

Cell lysates were prepared and immunoblotted using normalized samples of ~20 μg protein detected with monoclonal antibodies recognizing the intracellular segment of PTPμ (SK-7 or SK-18) (*Mol Cell Biochem* 1993; 127-128: 131-41). An antibody against vinculin was from Sigma-Aldrich (St. Louis, Mo.). The GFP antibody JL-8 was from Clontech (Mountain View, Calif.).

RT-PCR

The PCR primers were as follows:

```
extracellular forward
                                       (SEQ ID NO: 14)
(CGCGAATTCTAGAGACGTTCTCAGGTGGC), extracellular reverse
                                       (SEQ ID NO: 15)
(CCCGCAAGCTTACTTCTTCTCGCACTTG), intracellular forward
                                       (SEQ ID NO: 16)
(CGCGGATCCAAAGAGACCATGAGCAGCACCCGA),
and intracellular reverse
                                       (SEQ ID NO: 17)
(CCGGAATTCTCATCTGTTCTCATCTTTCTTAGCCGA).
```

Scratch Wound Assay

Confluent monolayers of cells were scratched to induce a wound and analyzed by microscopy for the distance migrated by the leading edge of the wound at 0 and 24 hrs.

Colony Formation Assays

Growth factor-independent clonogenic colony assays were performed as described (*Nat Protoc* 2006; 1: 2315-9). Crystal violet-stained colonies were imaged with the Quantity One imaging software of the Gel Doc imaging system (Bio-Rad, Hercules, Calif.). Images were quantitated using MetaMorph software (Molecular Devices) by measuring the thresholded area of each well to include only colonies. For the soft agarose assay, cells were seeded at a concentration of 75,000 cells/ml in 0.4% agarose and plated on an underlay of 0.8% agarose in a 6-well plate. Colonies were analyzed after four weeks by imaging Z-stacks of 20 random 10× fields using a Leica DMI6000B automated inverted microscope (Leica Microsystems GmbH, Wetzlar, Germany) attached to a Retiga EXi camera (QImaging, Surrey, BC, Canada). The number of colonies in minimized Z-stacks from each microscope field was recorded.

Biotinylation of Cell Surface Proteins

Cell surface biotinylation was performed using a Sulfo-NHS-SS-Biotin Kit (Pierce). Biotinylated proteins were isolated and resolved by SDS-PAGE on 6% gels followed by immunoblotting with an antibody to PTPμ (SK-18) as described (Mol Cancer Res 2008; 6: 1106-13).

Inhibitors

The Furin Inhibitor I (Dec-RVKR-CMK, Calbiochem, Gibbstown, N.J.) was used at 50 μM for 17-20 hours. The γ-secretase inhibitors DAPT (Sigma-Aldrich) and L-685,458 (Sigma-Aldrich) were used at 2 μM and 5 μM, respectively, for 17-20 hours. The proteasome was inhibited with MG132 (Sigma-Aldrich) at 20 μM or epoxomicin (Calbiochem) at 5 μM for 4 hours. GM6001 (Calbiochem) was used at 50 μM as an MMP/ADAM inhibitor for 17-20 hours. Inhibitors were reconstituted in DMSO, which was used as a vehicle control. An inhibitor of PTPμ function targeting the helix-loop-helix wedge domain has been demonstrated to inhibit PTPμ function (*J Biol Chem* 2006; 281: 16482-92; *Mol Cell Neurosci* 2007; 34: 481-92). The PTPμ wedge peptide and a scrambled control peptide were synthesized to include a membrane-penetrant Tat-derived sequence at the C-terminus to promote cellular uptake. Peptides synthesized by Genemed Synthesis (San Antonio, Tex.) or GenScript (Piscataway, N.J.) were reconstituted in water and added to cells at a final concentration of 5 μM.

Immunoprecipitations

Cells were grown to confluence, treated with inhibitors, and lysed in 20 mM Tris-HCL, pH 7.5, 1% Triton X-100, 150 mM NaCl, 2 mM EDTA, 1 mM benzamidine, aprotinin (5 μg/ml), leupeptin (5 μg/ml) and pepstatin (1 μg/ml). Samples were sonicated and centrifuged at 10,000 rpm for 5 minutes. Immunoprecipitations from ~400 μg total protein were performed using a PTPμ antibody (SK-18) and resolved by SDS-PAGE on 8% gels followed by immunoblotting with an antibody to PTPμ (SK-7).

Immunocytochemistry

Immunofluorescent cell staining was performed. Fixed cells were probed with SK-7 or SK-18, which recognize intracellular PTPμ, and detected with goat anti-mouse-Alexa 488 secondary antibody (Molecular Probes, Invitrogen). Slides were mounted with Citifluor Antifadent mounting medium (Electron Microscopy Sciences, Hatfield, Pa.) and imaged using the Leica system described above.

Tumor Specimens

Fresh human brain and tumor tissue were obtained from surgical resections in accordance with an approved protocol from the University Hospitals Case Medical Center Institutional Review Board. GBM specimens of approximately 100 mg each were obtained for protein extraction. Noncancerous, non-eloquent, cortical brain was also collected.

GBM xenograft tumors were grown in NIH athymic nude female mice in accordance with an approved protocol from the Case Western Reserve University Institutional Animal Care and Use Committee. LN-229 or Gli36Δ5 cells (2×106 cells) were resuspended in a 1:1 dilution of Matrigel (BD Biosciences; Franklin Lakes, N.J.) in PBS and were injected subcutaneously in the right flank region of the mouse. Tumors were harvested between 9-28 days after injection. Lysates of human and xenograft tumor specimens were prepared. Tumor samples were homogenized using a tissue tearor homogenizer or a 2 ml dounce homogenizer. Cleared lysates (about 20 μg from human samples and ~50 μg from xenograft samples) were analyzed by immunoblot on 8% gels with an antibody to PTPμ (SK-18).

Results

PTPμ Protein is Downregulated in the Human Glioblastoma Cell Line LN-229

PTPμ was overexpressed in LN-229 cells via a lentiviral construct, and both the full-length and normally produced P-subunit were detected by immunoblotting with an intracellular antibody to PTPμ (FIG. 9A). Lentiviral overexpression of PTPμ generated doublets at molecular weights corresponding to both full-length and P-subunit PTPμ (FIG. 9A). These doublets likely are due to post-translational modifications. mRNA expression of PTPμ was examined by RT-PCR in both U-87 MG and LN-229 cells. U-87 MG cells expressed PTPμ transcript as expected. Surprisingly, PTPμ transcript was also detected in LN-229 cells despite their lack of PTPμ protein expression (FIG. 9B). PTPμ shRNA downregulated PTPμ transcript but did not affect control GAPDH (FIG. 9C). These data show that the downregulation of PTPμ in glioblastoma is due to a post-transcriptional mechanism.

Overexpression of PTPμ Suppresses Cell Migration and Growth Factor-Independent Cell Survival We showed in Example 1 that shRNA-mediated downregulation of endogenous PTPμ in U-87 MG cells promotes cell migration. Based on this data, we hypothesized that overexpression of PTPμ in LN-229 cells would suppress cell migration. We evaluated this hypothesis using a scratch wound assay. Confluent monolayers of LN-229 cells overexpressing either vector or PTPμ were scratched to form a wound. After 24 hours, control LN-229 cells at the leading edge of the wound migrated an average of 150 μm (FIG. 10A). However, LN-229 cells overexpressing PTPμ had impaired migration with a 3-fold reduction in the distance migrated (FIG. 10A). Additionally, overexpression of PTPμ induced a morphological change in LN-229 cells and made the cells noticeably elongated (FIG. 10A). Because this assay occurred over 24 hours, it was possible that changes in cell proliferation could account for the difference in wound size. To rule out this possibility, LN-229 cells infected with vector or PTPμ were labeled with propidium iodide and analyzed by flow cytometry. Flow cytometry revealed no significant changes in cell proliferation between the vector- and PTPμ-infected cells (data not shown). Therefore, we concluded that the difference in wound size was due to a decrease in migration resulting from PTPµ overexpression, indicating PTPµ suppresses migration of LN-229 glioblastoma cells.

Growth Factor-Independent Survival is a Hallmark of Tumorigenesis

To assess the effect of PTPµ overexpression on growth factor-independent survival, a colony formation assay was used. After two weeks of growth factor deprivation, control LN-229 cells formed abundant colonies (FIG. 10B). In contrast, overexpression of PTPµ reduced colony formation by 2-fold (FIG. 10B). Therefore, PTPµ overexpression suppresses migration in two-dimensional culture and reduces growth factor-independent survival in three-dimensional culture of glioblastoma cells.

Proteolysis of PTPµ Contributes to its Downregulation in Glioblastoma

Other receptor tyrosine phosphatases are sequentially cleaved by a furin-like protease, an ADAM-type matrix metalloproteinase (MMP), and a γ-secretase to release a soluble intracellular domain-containing fragments. Since GBMs are known to have upregulated proteases (*Nat Rev Cancer* 2003; 3: 489-501), we hypothesized that constitutive proteolysis of PTPµ may be the mechanism of PTPµ downregulation in GBM. We first determined whether full-length PTPµ could be detected in parental LN-229 cells. Since we cannot detect PTPµ in a total cell lysate of parental LN-229 cells, we biotinylated cell surface proteins and used avidin resin to enrich the pool of biotinylated cell surface proteins. Despite the lack of PTPµ in the total cell lysate, the biotinylated cell surface fraction contained trace amounts of PTPµ (FIG. 11A). PTPµ is known to be cleaved by a furin-like protease to generate the E- and P-subunits of PTPµ. As expected, treatment of cells with an inhibitor of furin activity resulted in an accumulation of full-length PTPµ (200 kDa) at the cell surface. These data imply there is a trace amount of endogenous PTPµ in LN-229 cells that is processed by proteolysis. Biotinylation of cell surface proteins from LN-229 cells overexpressing PTPµ showed a similar pattern of full-length PTPµ accumulation at the cell surface upon furin inhibition (FIG. 11A).

After furin cleavage, PTPκ, another PTPµ-subfamily member, is subsequently cleaved by α- and γ-secretases. We hypothesized that PTPµ is cleaved similarly. To test this hypothesis, LN-229 cells were treated with inhibitors of α- and γ-secretases. Proteasome inhibitors were used for biochemical detection to prevent rapid degradation of these fragments. Since we cannot detect PTPµ in whole cell lysates, the PTPµ fragments were immunoprecipitated from LN-229 cells treated with inhibitors using antibody to the intracellular domain of PTPµ. The γ-secretase inhibitor DAPT stabilized a fragment that corresponds by molecular weight to a membrane-tethered truncated P-subunit termed PΔE (FIG. 11B). Treatment with the proteasome inhibitor MG132 led to the accumulation of both PΔE and a soluble fragment termed PTPµ intracellular domain (ICD) (FIG. 11B). The MMP inhibitor GM6001 limited the formation of PTPµ PΔE and ICD fragments, indicating cleavage by an MMP is required for subsequent processing (FIG. 11B). MG132 has been reported to inhibit γ-secretase activity in addition to proteasome activity, leading to the accumulation of α- and γ-secretase products. Subsequent experiments included a more specific proteasome inhibitor, epoxomicin, to distinguish these events. Overall, these data support our hypothesis that the endogenous PTPµ expressed in LN-229 cells is constitutively cleaved to generate PTPµ PΔE and ICD. As a result, little full-length PTPµ is present to function at the cell surface in LN-229 cells.

Figure 11C:
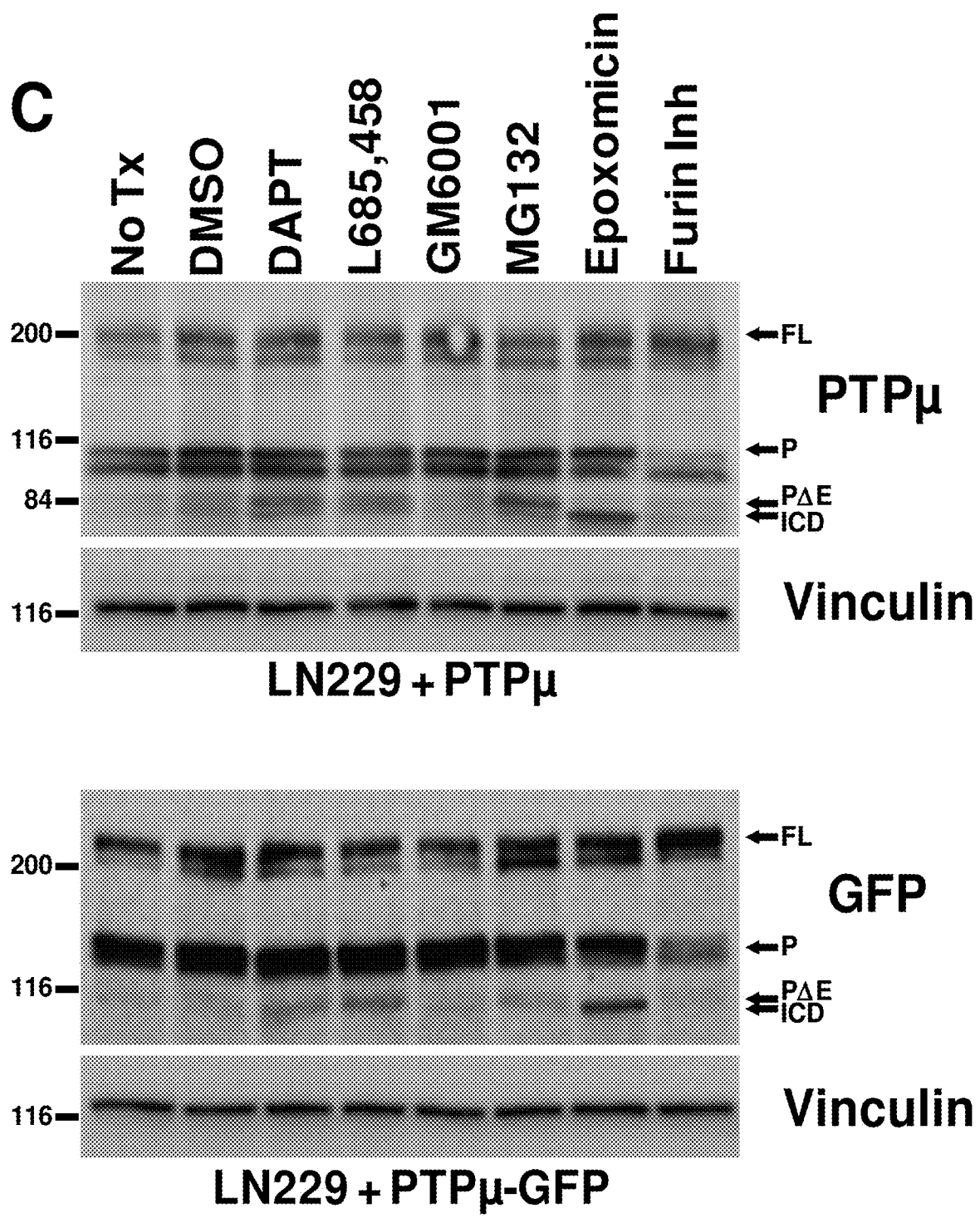
FIGS. 11(A-D) illustrate immunoblots and a schematic image showing PTPμ is proteolytically processed to release a catalytically active intracellular domain-containing fragments from the membrane. (A) Lysates from parental LN-229 cells and LN-229 cells overexpressing PTPμ were biotinylated and immunoblotted for PTPμ with an antibody against the intracellular segment of PTPμ (SK-18). Trace amounts of PTPμ protein were detected in cell surface-labeled LN-229 cells. Treatment with an inhibitor of furin prevented P-subunit formation. (B) LN-229 cells treated with protease inhibitors were immunoprecipitated with SK-18 and immunoblotted with an antibody against the juxtamembrane domain of PTPμ (SK-7). Proteolyzed membrane-associated (PΔE) and soluble (ICD) fragments of PTPμ were stabilized with γ-secretase (DAPT) and proteasome (MG132) inhibitors. (C) Lysates from LN-229 cells treated with specific protease inhibitors and overexpressing PTPμ or PTPμ-GFP were immunoblotted with SK-7 and GFP antibodies, respectively. PTPμ PΔE and ICD were stabilized with γ-secretase (DAPT, L685,458) and proteasome (MG132, epoxomicin) inhibitors. Vinculin was used as a loading control. (D) PTPμ is sequentially cleaved by a furin-like protease, an α-secretase (ADAM-type MMP), and a γ-secretase to generate a membrane-free ICD that translocates to the nucleus.
Figure 11D:
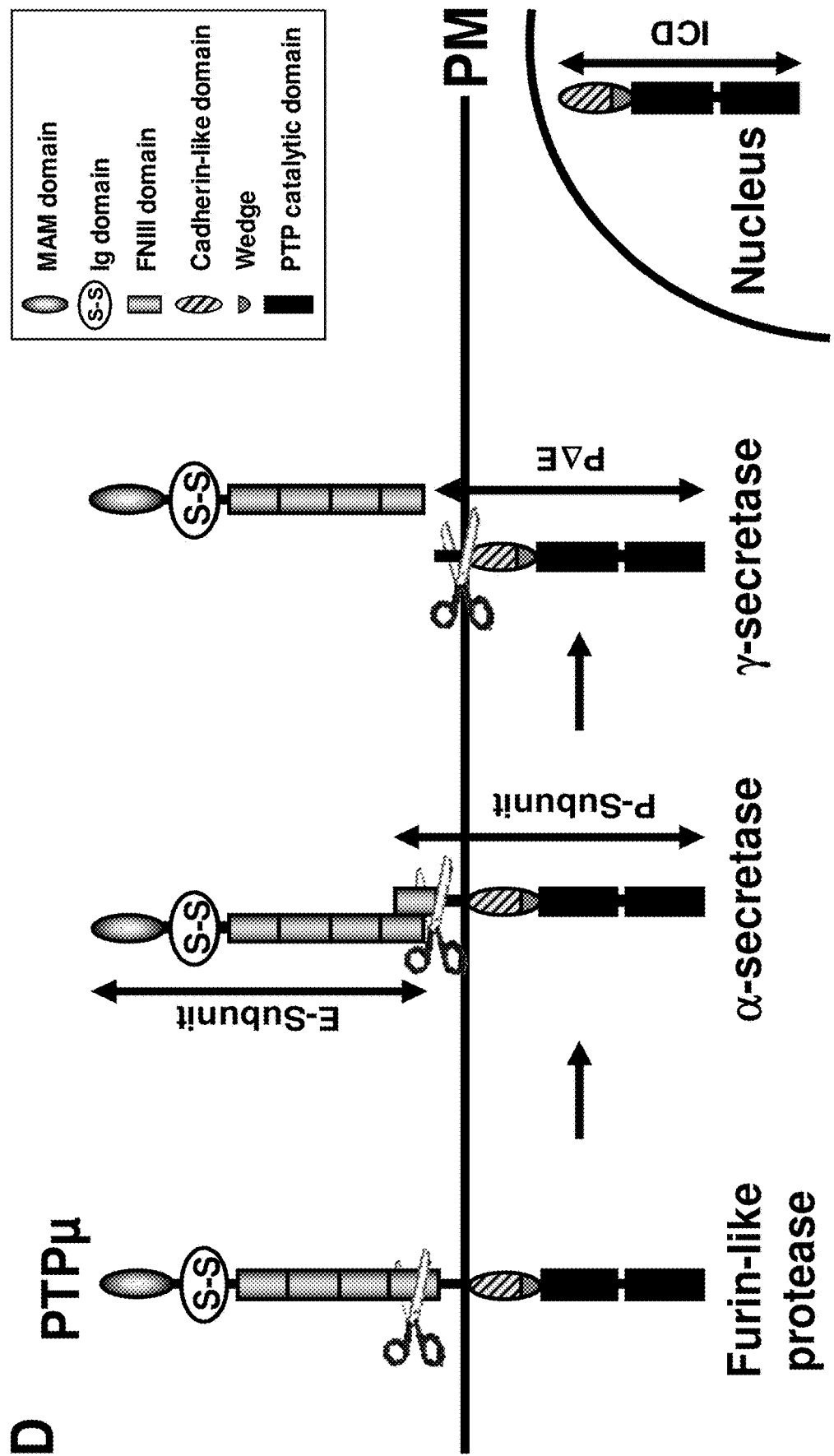

Total cell lysates from LN-229 cells overexpressing PTPµ showed a similar pattern of cleavage products upon inhibitor treatment (FIG. 11C). Stabilization of PTPµ ICD with treatment of epoxomicin confirmed that this fragment is labile and can only be seen when stabilized by the addition of a proteasome inhibitor. Treatment with MG132 and γ-secretase inhibitors (DAPT and L685,458) showed accumulation of PTPµ PΔE and ICD (FIG. 11C). To verify the cleavage products include the C-terminus of the intracellular domain of PTPµ, we overexpressed a PTPµ construct with a C-terminal GFP-tag (PTPµ-GFP) in LN-229 cells. Cells expressing PTPµ-GFP were treated with inhibitors as above, and total cell lysates were immunoblotted with GFP to detect the PTPµ-GFP fragments. A GFP antibody detected a similar pattern of fragments, suggesting PTPµ PΔE and ICD fragments include the C-terminus of PTPµ (FIG. 11C). These data support the model depicted in FIG. 11D. Full-length PTPµ is cleaved by a furin-like protease to generate the E- and P-subunits in "normal" proteolytic processing. Cleavage by an ADAM-type MMP (α-secretase) in GBM cells generates PTPµ PΔE. Subsequently, PΔE is cleaved by γ-secretase to generate PTPµ ICD.

Figure 12A:
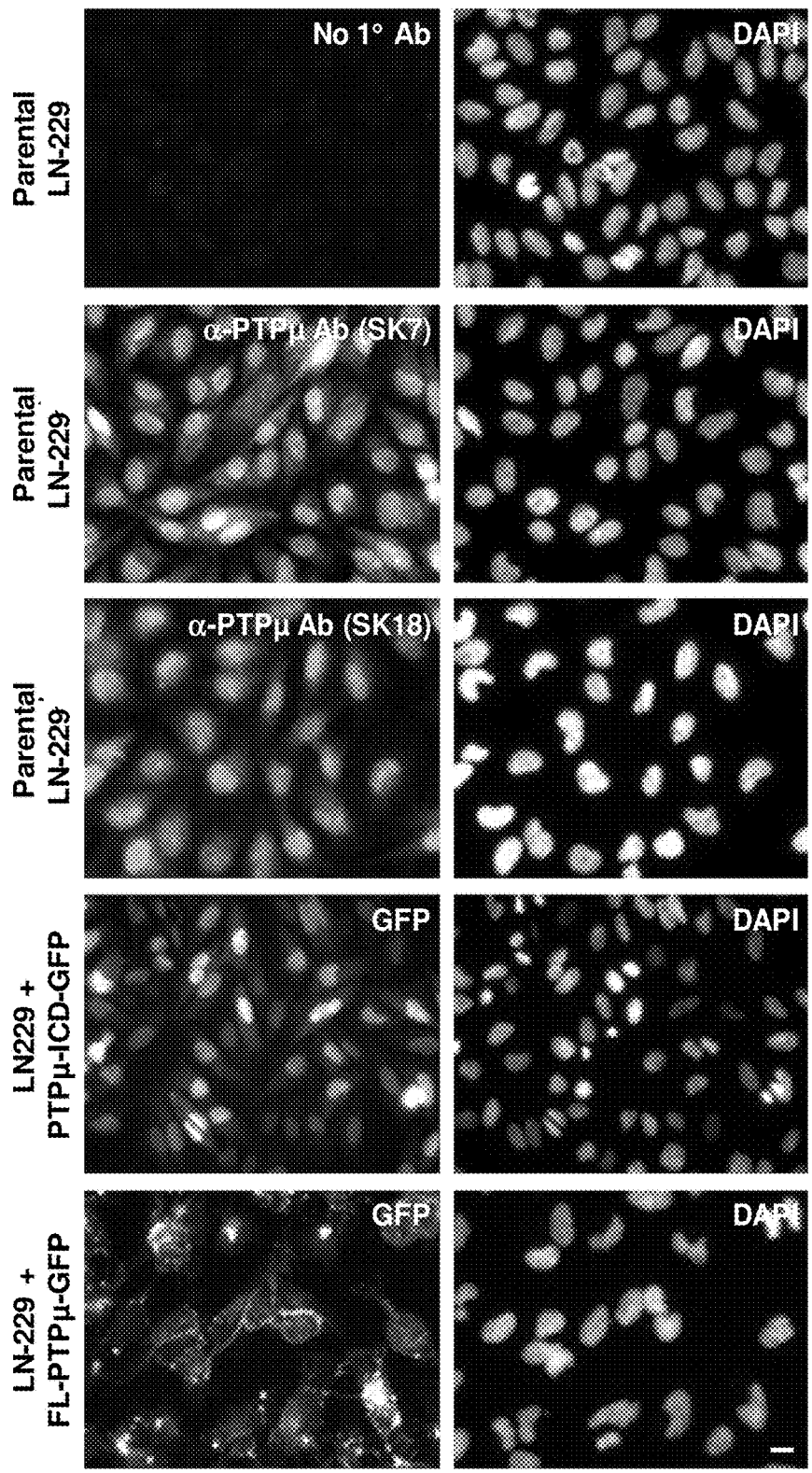
FIGS. 12(A-C) illustrate images showing PTPμ ICD localizes to the nucleus, and PΔE and ICD are expressed in human glioblastoma tumors and glioblastoma xenografts. (A) LN-229 cells expressing endogenous ICD were analyzed by immunocytochemistry using intracellular antibodies to PTPμ (SK-7 and SK-18). LN-229 cells overexpressing GFP-tagged PTPμ ICD or full-length PTPμ were also examined. The scale bar represents 20 μm. (B) PTPμ expression in human normal brain and glioblastoma tissue from four patients was analyzed by immunoblotting with SK-18. Vinculin was used as a loading control. (C) PTPμ PΔE and ICD expression was analyzed in LN-229 and Gli36Δ5 xenografts from mouse flank by immunoblotting with SK-18. A human GBM tumor (T) was loaded at the end for comparison. Vinculin was used as a loading control. The human GBM tumor specimen was loaded with 2-fold less protein, as its PTPμ PΔE and ICD expression is significantly higher than that of the xenograft specimens (see vinculin lane).

PTPµ ICD is a soluble fragment that translocates to the nucleus in another cell type (*J Cell Biochem* 2008; 105: 1059-72). To determine the subcellular localization of PTPµ ICD in glioblastoma cells, we performed immunocytochemistry on LN-229 cells. Antibodies recognizing the juxtamembrane (SK-7) and first phosphatase (SK-18) domains of PTPµ detected an endogenous PTPµ species with a nuclear pattern of localization similar to DAPI-stained nuclei (FIG. 12A). The epitopes of these antibodies suggest that this species is PTPµ ICD. Overexpression of GFP-tagged PTPµ ICD also localized to the nucleus and confirmed these findings. In contrast, overexpression of GFP-tagged full-length PTPµ resulted in a cell-cell contact and filopodial staining pattern. Full-length PTPµ likely senses extracellular adhesive cues to suppress migration by contact inhibition, whereas PTPµ ICD distributes to the cytoplasm and nucleus. These data suggest that full-length PTPµ and PTPµ ICD have distinct localization patterns, potentially leading to differences in their downstream signaling.

Intracellular Domain-Containing Fragments of PTPµ are Expressed in Human Glioblastoma Tumors and Glioblastoma Xenograft Tumors We demonstrated in Example 1 that PTPµ protein expression is downregulated in human GBM tumor samples. However, immunoblotting fresh GBM tumor tissue lysates on higher percentage gels indicated that fragments of PTPµ corresponding to PTPµ PΔE and ICD are expressed in human GBM tumor samples in comparison to normal brain tissue from the same patient (FIG. 12B). Full-length PTPµ was undetectable in these GBM tumor samples (FIG. 12B). PTPµ PΔE and ICD were identified in normal tissue samples that retain significant expression of full-length PTPµ (FIG. 12B). Therefore, it is the expression of full-length PTPµ that differs between normal brain and GBM tumor tissue. Normal brain tissue expresses full-length PTPµ, whereas GBM tumor tissue does not express full-length PTPµ but retains PTPµ PΔE and ICD.

Neither full-length PTPµ nor PTPµ PΔE and ICD are detectable in LN-229 total cell lysates by immunoblot. We assessed human GBM cell line tumor xenografts grown in mouse flanks to determine if the three-dimensional architecture of the tumor would stabilize PTPµ fragments in the GBM cells. Flank tumor lysates from LN-229 xenografts expressed little detectable full-length PTPµ but expressed abundant PTPµ PΔE and ICD (FIG. 12C). Similar results were obtained using xenografts prepared with another glioma cell line, Gli36Δ5 (FIG. 12C). These data show that three-dimensional human glioblastoma tumors and in vivo glioblastoma tumor models favor PTPμ proteolysis and stabilize PTPμ ICD and its precursor, PΔE, in vivo.

PTPμ Fragments Contribute to Glioblastoma Cell Migration and Both Growth Factor-Independent and Anchorage-Independent Cell Survival PTPμ ICD is a soluble fragment generated from PΔE that translocates to the nucleus (FIG. 12A). PTPμ ICD contains the catalytic domain of PTPμ and has the potential to signal differently than that of membrane-bound, cell surface-associated PTPμ due to changes in substrate availability in different cellular compartments. Overexpression of membrane-bound, cell surface-associated PTPμ suppressed GBM cell migration and growth factor-independent survival (FIG. 10). We hypothesized that PTPμ ICD and its precursor, PΔE, may signal differently and affect the migration and growth factor-independent survival of GBM cells. First, the effect of PTPμ fragments on cell migration was analyzed using a scratch wound assay.

Figure 13A:
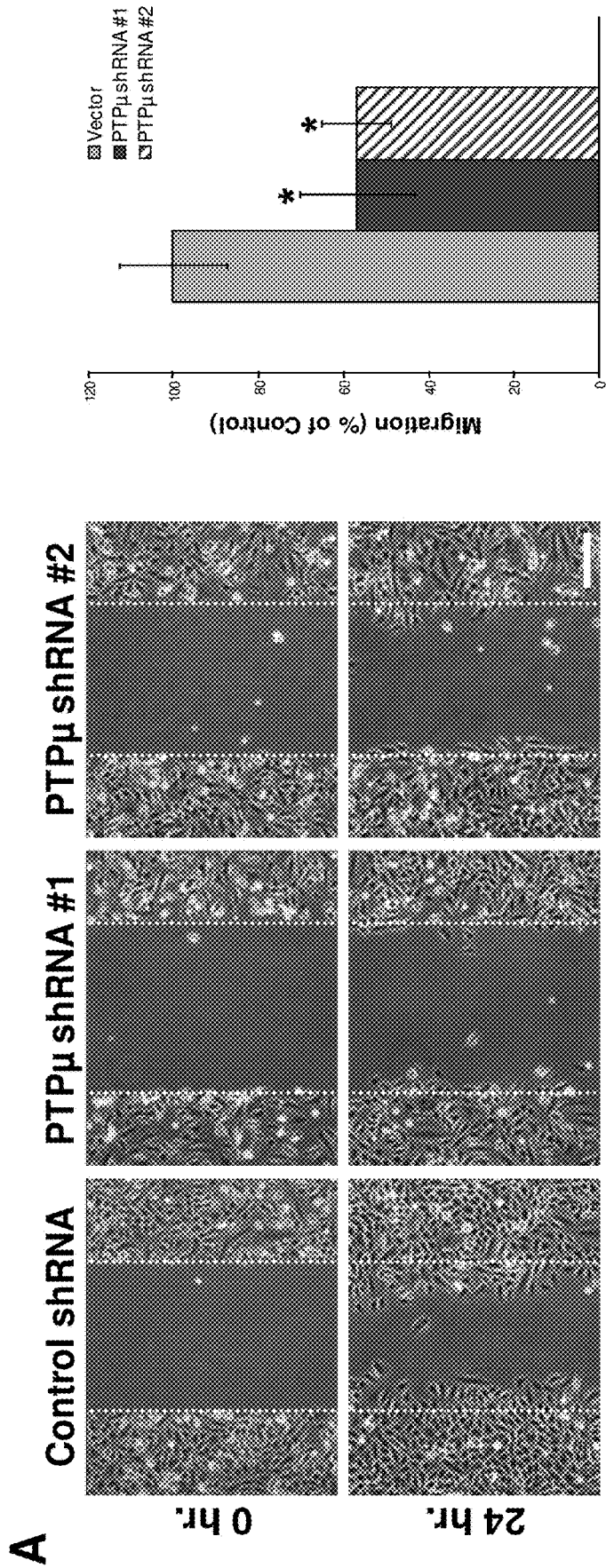
FIGS. 13(A-C) illustrate images showing PTPμ fragments contribute to glioblastoma cell migration and both growth factor- and anchorage-independent cell survival. (A) Confluent monolayers of LN-229 cells expressing control or PTPμ shRNA constructs were scratched and imaged at 0 and 24 hours. Dashed lines indicate the position of the wounded edge at 0 hours. The scale bar represents 200 μm. Asterisks indicate a statistically significant reduction in migration (PTPμ shRNA #1, n=4; PTPμ shRNA #2, n=6; p<0.05). (B)

PTPμ mRNA is expressed in LN-229 cells, but the only detectable proteins are PTPμ fragments (FIGS. 9, 11 and 12). Therefore, we were able to use shRNA to downregulate PTPμ fragments. Confluent monolayers of LN-229 cells expressing either control or two different PTPμ shRNA constructs were scratched and allowed to migrate (FIG. 13A). Downregulation of PTPμ fragments by both shRNA constructs suppressed cell migration by 2-fold (FIG. 13A). To rule out changes in cell proliferation, LN-229 cells infected with control or PTPμ shRNA were labeled with propidium iodide and analyzed by flow cytometry. No significant changes in cell proliferation were detected (data not shown).

Both PTPμ PΔE and ICD are partially stabilized by the γ-secretase inhibitor DAPT and are not formed when ADAMs are inhibited (FIG. 11). These inhibitors were used in a scratch wound assay to analyze their effects on PTPμ fragment-mediated cell migration. Stabilization of PTPμ fragments with DAPT increased migration and prevention of PTPμ fragment formation by GM6001 decreased migration. These data show that proteolysis of PTPμ promotes LN-229 cell migration.

Because PTPμ overexpression affected growth factor-independent cell survival, we hypothesized that PTPμ fragments may also affect cell survival. To test this hypothesis, LN-229 cells expressing control or PTPμ shRNA were seeded at low density and allowed to form colonies over two weeks (FIG. 13B). Downregulation of PTPμ fragments via shRNA reduced the number of colonies in comparison to control cells by 3-fold (FIG. 13B). These findings were confirmed in a soft agarose assay for anchorage-independent survival. PTPμ shRNA reduced the number of colonies in this assay by 5-fold (FIG. 13C). These data show PTPμ fragments promote both cell migration and growth factor-independent survival of glioblastoma cells.

Catalytic Activity of PTPμ Fragments is Required for Glioblastoma Cell Migration Soluble intracellular PTPμ has been demonstrated to retain catalytic activity. To examine whether the catalytic activity of PTPμ fragments is important in the regulation of cell migration, PTPμ function was inhibited using a PTPμ-specific peptide inhibitor. Confluent monolayers of LN-229 cells were treated with a membrane-penetrant PTPμ wedge peptide or a control scrambled peptide prior to scratching to induce a wound (FIG. 14). The PTPμ wedge peptide significantly reduced migration of LN-229 cells (FIG. 14). This suppression is likely due to inhibition of the signaling of the PTPμ fragments, as they are the only detectable PTPμ protein stabilized in LN-229 cells (FIG. 12). These data show that PTPμ fragments must be catalytically active to induce GBM cell migration. Therefore, the wedge peptide inhibitor of PTPμ may have therapeutic value in the treatment of human glioblastoma.

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

Having described the invention, the following is claimed:

1. A method of inhibiting in a subject one or more of motility, migration, invasion, dispersal, and metastasis of cells that express PTPμ that is proteolytically cleaved to produce intracellular domain-containing fragments, the method comprising:
administering to the cells expressing proteolytically cleaved intracellular domain-containing fragments of PTPμ in the subject an amount of a therapeutic agent effective to inhibit function of the proteolytically cleaved intracellular domain-containing fragments of the PTPμ, the therapeutic agent comprising a RNAi construct that reduces or inhibits the expression of the PTPμ in the cells.

2. The method of claim 1, the cells comprising cancer cells.

3. The method of claim 2, the cancer cells being a glioma, lung cancer, melanoma, breast cancer, prostate cancer or tumor-derived endothelial vessel cells.

4. The method of claim 2, the glioma being a glioblastoma multiforme.

5. The method of claim 1, the RNAi construct comprising interfering RNA that reduces or inhibits expression of PTPμ in cancer cells.

6. The method of claim 1, the RNAi construct comprising an RNAi expression vector that expresses siRNA or shRNA, which reduces or inhibits expression of PTPμ in cancer cells, upon administration to the cancer cells.

7. The method of claim 1, the therapeutic agent being conjugated to a targeting moiety to facilitate targeting of the therapeutic agent to the cells, where the targeting moiety is substantially homologous to a homophilic binding portion of a proteolytically cleaved extracellular fragment of the PTPμ.

8. The method of claim 7, the targeting moiety comprising a peptide that specifically binds to an amino acid sequence of SEQ ID NO: 18.

9. The method of claim 7, the targeting moiety comprising a peptide having an amino acid sequence that is substantially homologous to about 10 to about 50 consecutive amino acids of SEQ ID NO: 19.

10. The method of claim 7, the targeting moiety being a peptide having an amino acid sequence selected from the group consisting of SEQ ID NO: 20, SEQ ID NO: 21, SEQ ID NO: 22, and SEQ ID NO: 23.

11. A method of inhibiting in a subject one or more of motility, migration, invasion, dispersal, and metastasis of cancer cells that express PTPμ that is proteolytically cleaved to produce intracellular domain-containing fragments, the method comprising:
administering to the cancer cells expressing proteolytically cleaved intracellular domain-containing fragments of PTPμ in the subject an amount of a therapeutic agent effective to inhibit function of the proteolytically cleaved intracellular domain-containing fragments of the PTPμ, the therapeutic agent comprising a RNAi construct that reduces or inhibits the expression PTPμ in the cancer cells.

12. The method of claim 11, the cancer cells being glioma, lung cancer, melanoma, breast cancer, prostate cancer or tumor-derived endothelial vessel cells.

13. The method of claim 12, the glioma being a glioblastoma multiforme.

14. The method of claim 11, the RNAi construct comprising interfering RNA that reduces or inhibits expression of PTPμ in the cancer cells.

15. The method of claim 11, the RNAi construct comprising an RNAi expression vector that expresses siRNA or shRNA, which reduces or inhibits expression of PTPμ in cancer cells, upon administration to the cancer cells.

16. The method of claim 11, the therapeutic agent being conjugated to a targeting moiety to facilitate targeting of the therapeutic agent to the cancer cells, where the targeting moiety is substantially homologous to a homophilic binding portion of a proteolytically cleaved extracellular fragment of the PTPμ.

17. The method of claim 16, the targeting moiety comprising a peptide that specifically binds to an amino acid sequence of SEQ ID NO: 18.

18. The method of claim 16, the targeting moiety comprising a peptide having an amino acid sequence that is substantially homologous to about 10 to about 50 consecutive amino acids of SEQ ID NO: 19.

19. The method of claim 16, the targeting moiety being a peptide having an amino acid sequence selected from the group consisting of SEQ ID NO: 20, SEQ ID NO: 21, SEQ ID NO: 22, and SEQ ID NO: 23.

20. A method of treating invasive or metastatic cancer in a subject, the method comprising:
administering to cancer cells expressing proteolytically cleaved PTPμ intracellular domain-containing fragments of the subject an RNAi construct that reduces or inhibits the expression of the PTPμ in the cells at an amount effective to inhibit function of the proteolytically cleaved intracellular domain-containing fragments of the PTPμ.

21. The method of claim 20, the cancer cells being glioma, lung cancer, melanoma, breast cancer, or prostate cancer cells.

22. The method of claim 21, the glioma being a glioblastoma multiforme.

23. The method of claim 20, the RNAi construct comprising interfering RNA that reduces or inhibits expression of PTPμ in cancer cells.

24. The method of claim 20, the RNAi construct comprising an RNAi expression vector that expresses siRNA or shRNA, which reduces or inhibits expression of PTPμ in cancer cells, upon administration to the cancer cells.

25. The method of claim 20, the RNAi construct being conjugated to a targeting moiety to facilitate targeting of the RNAi construct to the cancer cells, where the targeting moiety is substantially homologous to a homophilic binding portion of a proteolytically cleaved extracellular fragment of the PTPμ.

26. The method of claim 25, the targeting moiety comprising a peptide that specifically binds to an amino acid sequence of SEQ ID NO: 18.

27. The method of claim 25, the targeting moiety comprising a peptide having an amino acid sequence that is substantially homologous to about 10 to about 50 consecutive amino acids of SEQ ID NO: 19.

28. The method of claim 25, the targeting moiety being a peptide having an amino acid sequence selected from the group consisting of SEQ ID NO: 20, SEQ ID NO: 21, SEQ ID NO: 22, and SEQ ID NO: 23.

* * * * *